(12) United States Patent
Tai et al.

(10) Patent No.: US 9,642,940 B2
(45) Date of Patent: May 9, 2017

(54) 3-DIMENSIONAL PARYLENE SCAFFOLD CAGE

(71) Applicants: CALIFORNIA INSTITUTE OF TECHNOLOGY, Pasadena, CA (US); UNIVERSITY OF SOUTHERN CALIFORNIA, Los Angeles, CA (US)

(72) Inventors: Yu-Chong Tai, Pasadena, CA (US); Bo Lu, Pasadena, CA (US); Mark Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 0 days.

(21) Appl. No.: 15/004,796

(22) Filed: Jan. 22, 2016

(65) Prior Publication Data
US 2016/0310637 A1    Oct. 27, 2016

Related U.S. Application Data

(63) Continuation of application No. 13/740,069, filed on Jan. 11, 2013, now Pat. No. 9,248,013, which is a
(Continued)

(51) Int. Cl.
*G03F 7/20* (2006.01)
*A61L 27/18* (2006.01)
(Continued)

(52) U.S. Cl.
CPC ............... *A61L 27/50* (2013.01); *A61F 2/02* (2013.01); *A61F 2/04* (2013.01); *A61L 27/025* (2013.01);
(Continued)

(58) Field of Classification Search
CPC .......... G03F 7/20; G03F 7/2002; A61L 27/18; A61L 27/3839; A61L 2420/02;
(Continued)

(56) References Cited

U.S. PATENT DOCUMENTS

| | | |
|---|---|---|
| 4,047,532 A | 9/1977 | Phillips et al. |
| 4,700,298 A | 10/1987 | Palcic et al. |

(Continued)

FOREIGN PATENT DOCUMENTS

| | | |
|---|---|---|
| AU | 2011279250 | 3/2015 |
| EP | 2593117 | 5/2013 |

(Continued)

OTHER PUBLICATIONS

U.S. Appl. No. 15/184,934, filed Jun. 16, 2016, Tai et al., including its prosecution history, the references and the Office Actions therein.
(Continued)

*Primary Examiner* — John A McPherson
(74) *Attorney, Agent, or Firm* — Knobbe, Martens, Olson & Bear LLP

(57) ABSTRACT

Thin parylene C membranes having smooth front sides and ultrathin regions (e.g., 0.01 μm to 5 μm thick) interspersed with thicker regions are disclosed. The back sides of the membranes can be rough compared with the smooth front sides. The membranes can be used in vitro to grow monolayers of cells in a laboratory or in vivo as surgically implantable growth layers, such as to replace the Bruch's membrane in the eye. The application further provides an implantable cage-like apparatus for culturing cells comprising the parylene membrane.

20 Claims, 18 Drawing Sheets

Related U.S. Application Data continuation-in-part of application No. 13/355,426, filed on Jan. 20, 2012, now Pat. No. 8,877,489.

(60) Provisional application No. 61/566,965, filed on Dec. 5, 2011, provisional application No. 61/586,276, filed on Jan. 13, 2012.

(51) Int. Cl.

| | | |
|---|---|---|
| *A61L 27/50* | (2006.01) | |
| *A61F 2/04* | (2013.01) | |
| *C12N 5/00* | (2006.01) | |
| *A61L 27/38* | (2006.01) | |
| *A61F 2/02* | (2006.01) | |
| *A61L 27/02* | (2006.01) | |
| *A61L 27/34* | (2006.01) | |

(52) U.S. Cl.
CPC .......... *A61L 27/18* (2013.01); *A61L 27/34* (2013.01); *A61L 27/3804* (2013.01); *A61L 27/3839* (2013.01); *C12N 5/0068* (2013.01); *G03F 7/2002* (2013.01); *A61F 2240/001* (2013.01); *A61L 2420/02* (2013.01); *A61L 2430/16* (2013.01); *C12N 2533/30* (2013.01)

(58) Field of Classification Search
CPC ...... A61L 27/3804; A61L 27/50; A61L 27/34; A61L 2430/16; C08L 65/04; C12N 2533/30; A61F 2240/001
USPC .... 430/320, 323, 324, 329; 427/2.24, 407.1, 427/255.6
See application file for complete search history.

(56) References Cited

U.S. PATENT DOCUMENTS

| | | | |
|---|---|---|---|
| 4,715,373 | A | 12/1987 | Mazzocco et al. |
| 5,024,223 | A | 6/1991 | Chow |
| 5,196,003 | A | 3/1993 | Bilweis |
| 5,843,780 | A | 12/1998 | Thomson |
| 6,117,675 | A | 9/2000 | van der Kooy et al. |
| 6,156,042 | A | 12/2000 | Aramant |
| 6,200,806 | B1 | 3/2001 | Thomson |
| 6,231,879 | B1 | 5/2001 | Li et al. |
| 6,254,628 | B1 | 7/2001 | Wallace et al. |
| 6,264,941 | B1 | 7/2001 | Baetge et al. |
| 6,299,895 | B1 | 10/2001 | Hammang et al. |
| 6,303,136 | B1 | 10/2001 | Li et al. |
| 6,322,804 | B1 | 11/2001 | Dionne et al. |
| 6,337,198 | B1 | 1/2002 | Levene et al. |
| 6,361,771 | B1 | 3/2002 | Tao et al. |
| 6,436,427 | B1 | 8/2002 | Hammang et al. |
| 6,582,903 | B1 | 6/2003 | Rigler et al. |
| 6,627,422 | B1 | 9/2003 | Li et al. |
| 6,642,048 | B2 | 11/2003 | Xu et al. |
| 6,649,184 | B2 | 11/2003 | Hammang et al. |
| 6,667,176 | B1 | 12/2003 | Funk et al. |
| 6,669,719 | B2 | 12/2003 | Wallace et al. |
| 6,712,837 | B2 | 3/2004 | Akerfeldt et al. |
| 6,800,480 | B1 | 10/2004 | Bodnar et al. |
| 6,833,269 | B2 | 12/2004 | Carpenter |
| 6,852,527 | B2 | 2/2005 | Chan et al. |
| 6,875,607 | B1 | 4/2005 | Reubinoff et al. |
| 6,939,378 | B2 | 9/2005 | Fishman et al. |
| 6,942,873 | B2 | 9/2005 | Russell et al. |
| 7,005,252 | B1 | 2/2006 | Thomson |
| 7,011,828 | B2 | 3/2006 | Reubinoff et al. |
| 7,029,913 | B2 | 4/2006 | Thomson |
| 7,107,124 | B2 | 9/2006 | Green |
| 7,115,257 | B1 | 10/2006 | Tao et al. |
| 7,135,172 | B1 | 11/2006 | Loftus et al. |
| 7,141,369 | B2 | 11/2006 | Cao |
| 7,147,648 | B2 | 12/2006 | Lin |
| 7,217,569 | B2 | 5/2007 | Thomson |
| 7,250,294 | B2 | 7/2007 | Carpenter et al. |
| 7,297,539 | B2 | 11/2007 | Mandalam et al. |
| 7,384,426 | B2 | 6/2008 | Wallace et al. |
| 7,410,798 | B2 | 8/2008 | Mandalam et al. |
| 7,413,734 | B2 | 8/2008 | Mistry et al. |
| 7,413,902 | B2 | 8/2008 | Bodnar et al. |
| 7,439,064 | B2 | 10/2008 | Thomson et al. |
| 7,455,983 | B2 | 11/2008 | Xu et al. |
| 7,504,257 | B2 | 3/2009 | Reubinoff et al. |
| 7,541,186 | B2 | 6/2009 | Reh et al. |
| 7,582,479 | B2 | 9/2009 | Thomson |
| 7,601,525 | B2 | 10/2009 | Batich et al. |
| 7,604,992 | B2 | 10/2009 | Reubinoff |
| 7,695,967 | B1 | 4/2010 | Russell et al. |
| 7,736,896 | B2 | 6/2010 | Klimanskaya et al. |
| 7,749,726 | B2 | 7/2010 | Chuck |
| 7,781,216 | B2 | 8/2010 | Thomson |
| 7,794,704 | B2 | 9/2010 | Klimanskaya et al. |
| 7,795,025 | B2 | 9/2010 | Klimanskaya et al. |
| 7,820,195 | B2 | 10/2010 | Kauper et al. |
| 7,824,671 | B2 | 11/2010 | Binder et al. |
| 7,838,727 | B2 | 11/2010 | Lanza et al. |
| 7,846,467 | B2 | 12/2010 | Coroneo |
| 7,855,068 | B2 | 12/2010 | Cao |
| 7,875,296 | B2 | 1/2011 | Binette et al. |
| 7,893,315 | B2 | 2/2011 | Chung et al. |
| 7,910,369 | B2 | 3/2011 | West et al. |
| 7,914,147 | B2 | 3/2011 | Sharifzadeh et al. |
| 7,947,498 | B2 | 5/2011 | Reubinoff et al. |
| 7,959,942 | B2 | 6/2011 | Cottone |
| 8,808,687 | B2 | 8/2014 | Humayun et al. |
| 8,877,489 | B2 | 11/2014 | Tai et al. |
| 9,248,013 | B2 | 2/2016 | Tai et al. |
| 2002/0160509 | A1 | 10/2002 | Reubinoff et al. |
| 2003/0054331 | A1 | 3/2003 | Fraser et al. |
| 2003/0083646 | A1 | 5/2003 | Sirhan et al. |
| 2003/0231791 | A1 | 12/2003 | Torre-Bueno et al. |
| 2005/0031599 | A1 | 2/2005 | Kooy et al. |
| 2005/0079616 | A1 | 4/2005 | Reubinoff |
| 2005/0106554 | A1 | 5/2005 | Palecek et al. |
| 2005/0164383 | A1 | 7/2005 | Reubinoff et al. |
| 2005/0214345 | A1 | 9/2005 | Leng et al. |
| 2005/0260747 | A1 | 11/2005 | Reubinoff et al. |
| 2006/0002900 | A1 | 1/2006 | Binder et al. |
| 2006/0078543 | A1 | 4/2006 | Reubinoff et al. |
| 2006/0078545 | A1 | 4/2006 | Carpenter |
| 2006/0104957 | A1 | 5/2006 | Yiu et al. |
| 2006/0149194 | A1 | 7/2006 | Conston et al. |
| 2006/0234376 | A1 | 10/2006 | Mistry et al. |
| 2006/0235430 | A1 | 10/2006 | Le et al. |
| 2006/0282128 | A1 | 12/2006 | Tai et al. |
| 2007/0106208 | A1 | 5/2007 | Uber et al. |
| 2007/0212777 | A1 | 9/2007 | Reubinoff |
| 2008/0243224 | A1 | 10/2008 | Wallace et al. |
| 2008/0299582 | A1 | 12/2008 | Mandalam et al. |
| 2009/0004736 | A1 | 1/2009 | Reubinoff |
| 2009/0074832 | A1 | 3/2009 | Zussman et al. |
| 2009/0075373 | A1 | 3/2009 | Reubinoff et al. |
| 2009/0104695 | A1 | 4/2009 | Shushan et al. |
| 2009/0117639 | A1 | 5/2009 | Carpenter |
| 2009/0123992 | A1 | 5/2009 | Chin |
| 2009/0130756 | A1 | 5/2009 | Klann et al. |
| 2009/0270982 | A1 | 10/2009 | Torres et al. |
| 2009/0291495 | A1 | 11/2009 | Carpenter et al. |
| 2009/0305405 | A1 | 12/2009 | Carpenter et al. |
| 2009/0306772 | A1 | 12/2009 | Tao et al. |
| 2010/0068141 | A1 | 3/2010 | Kaushal et al. |
| 2010/0093091 | A1 | 4/2010 | Reubinoff et al. |
| 2010/0137510 | A1 | 6/2010 | Seliktar et al. |
| 2010/0144033 | A1 | 6/2010 | Mandalam et al. |
| 2010/0173410 | A1 | 7/2010 | Thomson et al. |
| 2010/0189338 | A1 | 7/2010 | Lin et al. |
| 2010/0203633 | A1 | 8/2010 | Mandalam et al. |
| 2010/0211079 | A1 | 8/2010 | Aramant |
| 2010/0241060 | A1 | 9/2010 | Roizman et al. |
| 2010/0272803 | A1 | 10/2010 | Mistry et al. |
| 2010/0299765 | A1 | 11/2010 | Klimanskaya et al. |
| 2010/0317101 | A1 | 12/2010 | Mandalam et al. |

(56) References Cited

U.S. PATENT DOCUMENTS

| | | | |
|---|---|---|---|
| 2011/0004304 A1 | 1/2011 | Tao et al. | |
| 2011/0027787 A1 | 2/2011 | Chuck | |
| 2011/0053152 A1* | 3/2011 | Goldkorn | C12N 5/0693 |
| | | | 435/6.14 |
| 2011/0060232 A1 | 3/2011 | Lin et al. | |
| 2011/0076320 A1 | 3/2011 | Coroneo | |
| 2011/0091927 A1 | 4/2011 | Reubinoff et al. | |
| 2011/0117062 A1 | 5/2011 | Klimanskaya et al. | |
| 2011/0117063 A1 | 5/2011 | Klimanskaya et al. | |
| 2011/0177594 A1 | 7/2011 | Shushan et al. | |
| 2011/0189135 A1 | 8/2011 | Aharonowiz et al. | |
| 2011/0236464 A1 | 9/2011 | Coffey et al. | |
| 2011/0256623 A1 | 10/2011 | Thomson | |
| 2012/0083425 A1* | 4/2012 | George | C12N 5/0062 |
| | | | 506/10 |
| 2013/0137958 A1 | 5/2013 | Tai et al. | |
| 2014/0134607 A1* | 5/2014 | Lin | G01N 27/327 |
| | | | 435/5 |
| 2015/0032207 A1 | 1/2015 | Humayun et al. | |
| 2015/0147377 A1 | 5/2015 | Humayun et al. | |
| 2015/1478100 | 5/2015 | Tai et al. | |

FOREIGN PATENT DOCUMENTS

| | | |
|---|---|---|
| JP | 11-009297 | 1/1999 |
| JP | 5876045 | 1/2016 |
| WO | WO 2005/082049 | 9/2005 |
| WO | WO 2007/132332 | 11/2007 |
| WO | WO 2008/098187 | 8/2008 |
| WO | WO 2008/129554 | 10/2008 |
| WO | WO 2009/127809 | 10/2009 |
| WO | WO 2012/004592 | 1/2012 |
| WO | WO 2012/009377 | 1/2012 |
| WO | WO 2012/149468 | 11/2012 |
| WO | WO 2012/149480 | 11/2012 |
| WO | WO 2012/149484 | 11/2012 |

OTHER PUBLICATIONS

U.S. Appl. No. 14/498,918, filed Sep. 26, 2014, Yu-Chong Tai et al., including its prosecution history, the reference and the Office Actions therein.
U.S. Appl. No. 14/314,994, filed Jun. 25, 2014, Humayun, et al., including its prosecution history, the reference and the Office Actions therein.
U.S. Appl. No. 14/114,160, filed Oct. 25, 2013, Humayun, et al., including its prosecution history, the references and the Office Actions therein.
"12mm Transwell with 0.4 um Pore Polyester Membrane Insert," [Online], Corning. Com, URL:http://catalog2.corning.com/Lifesciences/en-US/Shopping/PFProductDetails.aspx?productid=3460(Lifesciences)>> [retrieved on Jun. 12, 2009].
Algvere et al., "Transplantation of RPE in Age-Related Macular Degeneration: Observations in Disciform Lesions and dry RPE Atrophy," Graefe's Arch Clin Exp Ophthalmol, vol. 235, Issue 3, 1997, pp. 149-158.
Binder S. et al., "Transplantation the RPE in AMD," Progress in Retinal and Eye Research, vol. 26, No. 5, Sep. 2007, pp. 516-554.
Chang et al., Cell and Protein Compatibility of Parylene-C Surfaces, Langmuir, vol. 23(23):11718-11725 (2007).
Deboer et al., "Multiparameter Analysis of Primary Epithelial Cultures Grown on Cyclopore Membranes," Journal of Histochemistry and Cytochemistry, vol. 42, Issue 2, 1994, pp. 277-282.
Hannachi et al., "Cell Sheet Technology and Cell Patterning for Biofabrication," Biofabrication [Online], vol. 1, No. 2, p. 022002, Jun. 10, 2009, URL:http://iopscience.iop.org/1758-5090/1/2/022002/ [Retrieved on Jul. 17, 2012].
Huang, Yiming, et al. "Stem cell-based therapeutic applications in retinal degenerative diseases" Stem Cell Reviews and Reports, Humana Press Inc., NY. vol. 7, No. 2, Sep. 22, 2009, pp. 434-445.
International Search Report in PCT/US2011/043747 (WO 2012/009377), dated Jul. 24, 2012.
Kannan R. et al., "Stimulation of Apical and Basolateral VEGF-A and VEGF-C Secretion by Oxidative Stress in Polarized Retinal Pigment Epithelial Cells," Molecular Vision, vol. 12, 2006, pp. 1649-1659.
Lavik, E. B. et al., "Fabrication of Degradable Polymer Scaffolds to Direct the Integration and Differentiation of Retinal Progenitors," Biomaterials, vol. 26, Issue 16, Jun. 2005, pp. 3187-3196.
Lu, Bo et al. "Semipermeable parylene membrane as an artificial bruch's membrane" 2011 16th International Solid-State Sensors, Actuators and Microssytems Conference (Transducers 2011): Beijing, China Jun. 5-9, 2011. pp. 950-953.
Lu, JT et al., Thin collagen film scaffolds for retinal epithelial cell culture, Biomaterials, vol. 28:1486-1494 (2007).
Morris et al., Cryopreservation of murine embryos, human spermatazoa and embryonic stem cells using a liquid nitrogen-free controlled rate freezer, Reproductive Biomedicine Online, vol. 13(3):421-426 (2006).
Pereira-Rodrigues et al., Modulation of hepatocarcinoma cell morphology and activity by parylene-C coating on PDMS, PLoS One, vol. 5(3):e9667 (2010).
Neeley, W. et al., "A Microfabricated Scaffold for Retinal Progenitor Cell Grafting," Biomaterials, vol. 29, Issue 4, Feb. 2008, pp. 418-426.
Redenti, S et al., "Engineering Retinal Progenitor Cell and Scrollable poly(glycerol-sebacate) composites for Expansion and Subretinal Transplantation," Biomaterials, vol. 30, Issue 20, Apr. 9, 2009, pp. 3405-3414.
Redenti, S et al., "Retinal Tissue Engineering using Mouse Retinal Progenitor Cells and a Novel Biodegradable, Thin-Film Poly(e-caprolactone) Nanowire Scaffold," J Ocul Biol Dis Infor., vol. 1, Issue 1, May 22, 2008, pp. 19-29.
Sodha, S. "A Microfabricated 3-D stem Cell Delivery Scaffold for Retinal Regenerative Therapy," Thesis, Master of Engineering in Biomedical Engineering, Massachusetts Institute of Technology, Jun. 2009.
Sodha, S. et al., "Microfabrication of a Three-Dimensional Polycaprolactone Thin-Film Scaffold for Retinal Progenitor Cell Encapsulation," J Biomater Sci Polym Ed., vol. 22, Issue 4-6, Jun. 21, 2011, pp. 443-456.
Stanzel B. V. et al., "Culture of Human RPE from Aged Donors on a Potential Bruch's Membrane Prosthesis" Invest Ophthalmol Vis Sci, [Online] vol. 47, 2006, URL:http://abstracts.iovs.org/cgi/content/abstract/47/5/1407?maxtoshow=&HITS=10&hits=10
&RESULTFORMAT=1&author1=stanzel&andorexacttitle=and
&andorexacttitleabs=and&andorexactfulltext=and&searchid=1
&FIRSTINDEX=O&sortspec=relevance
&resourcetype=HWCIT,HWELT R> [retrieved on Jun. 12, 2009].
Stanzel et al., "Towards Prosthetic Replacement of Bruch's Membrane: Comparison of Polyester and Electrospun Nanofiber Membranes" Invest Ophthalmol Vis Sci, [Online] vol. 48, 2007, URL:http://abstracts.iovs.org/cgi/content/abstract/48/5/5085?maxtoshow=&HITS=10&hits=10&RESULTFORMAT=1
&author1=stanzel&andorexacttitle=and&andorexacttitleabs=and
&andorexactfulltext=and&searchid=1&FIRSTINDEX=O
&sortspec=relevance&resourcetype=HWCIT,HWELT R> [retrieved on Jun. 12, 2009].
Tezcaner, A et al., "In Vitro Characterization of Micropatterned PLGA-PHBV8 Blend Films as Temporary Scaffolds for Photoreceptor Cells," J Biomed Mater Res vol. 86A, Issue 1, Oct. 23, 2007, pp. 170-181.
Wang, Renxin, et al. "Fabrication and characterization of a parylene-based three-dimensional microelectrode array for use in retinal prosthesis" Journal of Microelectromechanical Systems, IEEE Service Center, US, vol. 19, No. 2, Apr. 1, 2010 pp. 367-374.
IPRP and Written Opinion of the International Search Authority in PCT/US2011/043747 (WO 2012/009377), dated Jan. 15, 2013.
Armstrong et al., "The hydrodynamic radii of macromolecules and their effect on red blood cell aggregation," Biophys J., vol. 87:4259-4270 (2004).

(56) References Cited

OTHER PUBLICATIONS

Hsiao et al. Microfluidic system for formation of PC-2 prostate cancer co-culture spheroids, Biomaterials, vol. 30:3020-3027 (2009).
Humayun et al, Biocompatible substrate for facilitating interconnections between stem cells and target tissues and methods for implanting same U.S. Appl. No. 61/481,037, filed Apr. 29, 2011.
Jackson et al., Human retinal molecular weight exclusion limit and estimate of species variation, IOVS, vol. 44:2141-2146 (2003).
Lee et al., Determination of human lens capsule permeability and its feasibility as a replacement for Bruch's membrane, Biomaterials, vol. 27:1670-1678 (2006).
Liu et al., A 3-D microfluidic combinatorial cell culture array, IEEE Proce of MEMS, Sorrento Italy, pp. 427-430 (2009).
Lu, Bo et al., "A 3D parylene scaffold cage for culturing retinal pigment epithelial cells," Micro Electro Mechanical Systems (MEMS), 2012, Paris, Italy, pp. 741-744.
Lu, et al., A study of the autofluorescence of parylene materials for micro-TAS applications, Lab Chip, vol. 10:1826-1834 (2010).
Lu, et al., Ultra-thin parylene-C semipermeable membranes for biomedical applications, IEEE International Micro Electro Mechanical Systems (MEMS '11) Cancun, Mexico, Jan. 23-27, 2011, pp. 505-508.
Lu, Bo et al., "Mesh-supported submicron parylene-C membranes for culturing retinal pigment epithelial cells," Biomed Microdevices, 2012, vol. 14, pp. 659-667.
Roy, et al., Silicon nanopore membrane technology for an implantable artificial kidney, Proc. of Tranducers, Denver Colorado, pp. 755-760 (2009).
U.S. Appl. No. 13/355,426, filed Jun. 6, 2013, Yu-Chong Tai et al., including its prosection history, the references and the Office Actions therein.
U.S. Appl. No. 13/181,279, filed Jan. 12, 2012, Humayun, et al., including its prosection history, the reference and the Office Actions therein.
U.S. Appl. No. 13/740,069, filed Jan. 11, 2013, Yu-Chong Tai et al., including its prosection history, the references and the Office Actions therein.
Chong, N.H. Victor et al. Management of inherited outer retinal dystrophies: present and future. Br J Ophthalmoi 1999:83:120-122.
Extended European Search Report dated Dec. 5, 2013 for EP 11 80 7411.
Written Opinion of the International Search Authority in PCT/US2011/043747 (WO 2012/009377), dated Jul. 24, 2012.

* cited by examiner

TOP VIEW WITH CELLS

TOP VIEW

BOTTOM VIEW

TOP VIEW

BOTTOM VIEW

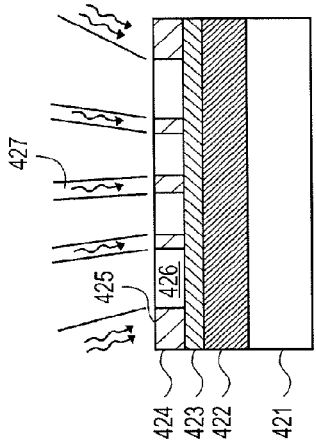
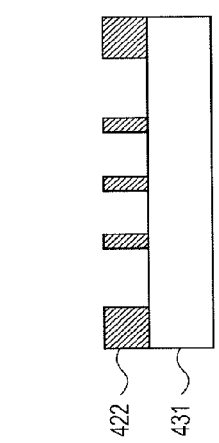
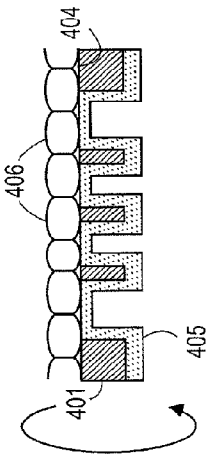
FIG. 4A  FIG. 4B  FIG. 4C
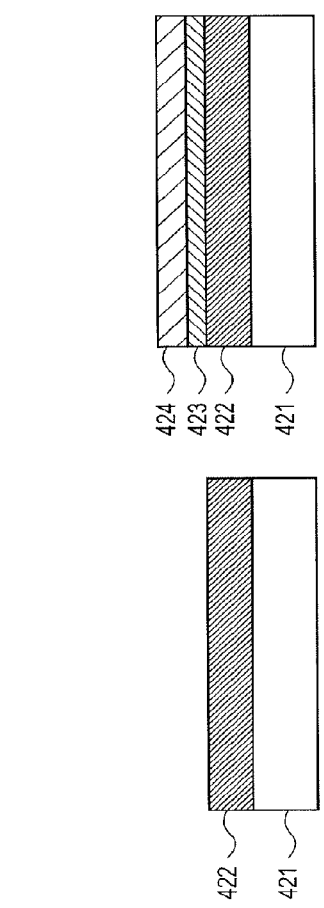
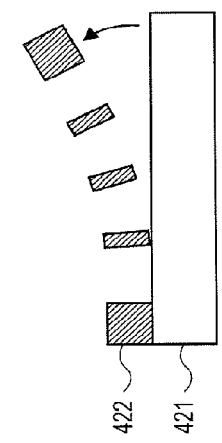
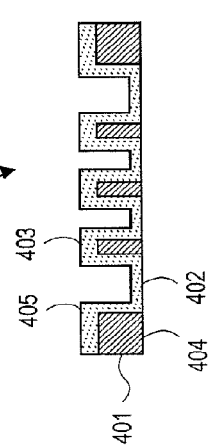
FIG. 4D  FIG. 4E  FIG. 4F
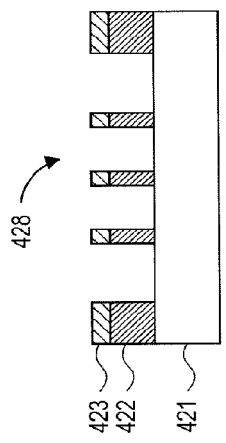
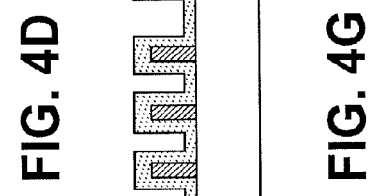
FIG. 4G  FIG. 4H  FIG. 4I

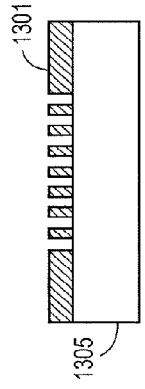
FIG. 13A
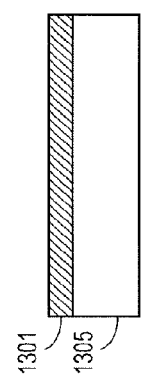
FIG. 13D
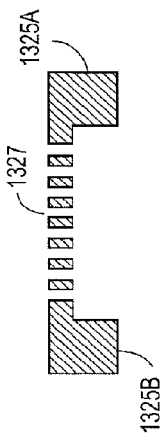
FIG. 13B
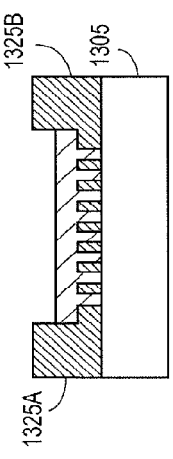
FIG. 13E
FIG. 13C
FIG. 13F
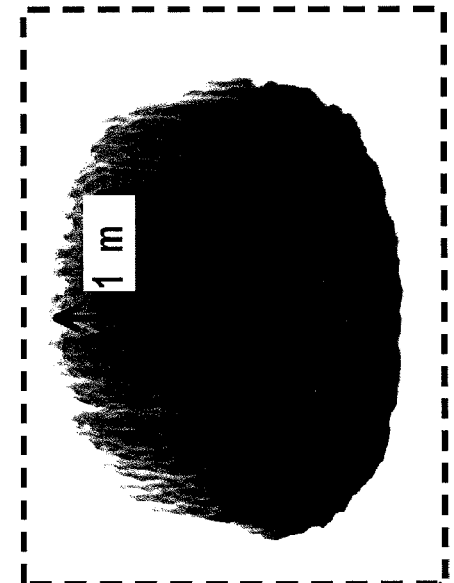
FIG. 13G
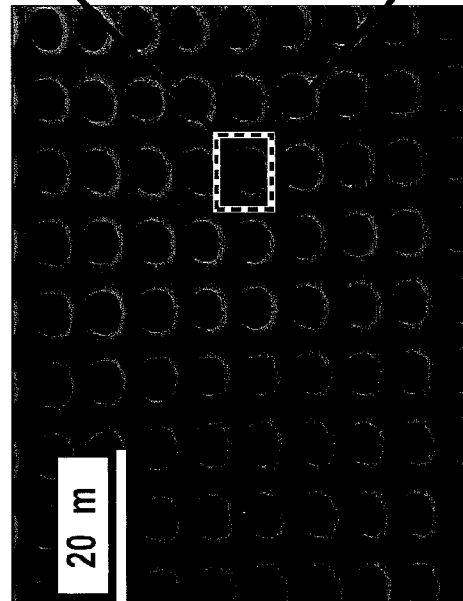
FIG. 13H 0 week
Plastic ring
Parylene ring 1 week
Matrigel 1 week 4 weeks

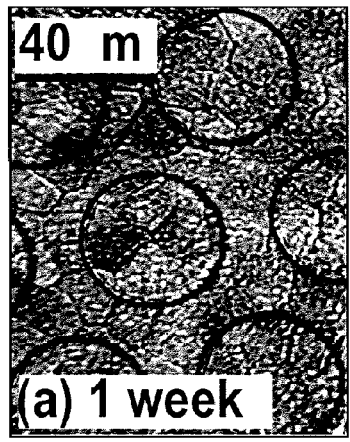
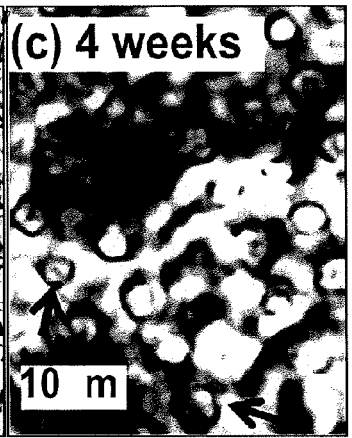
FIG. 19A     FIG. 19B     FIG. 19C
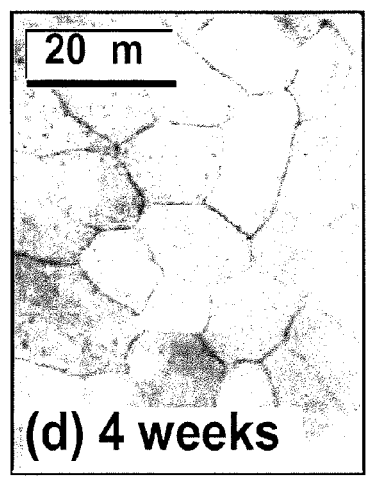
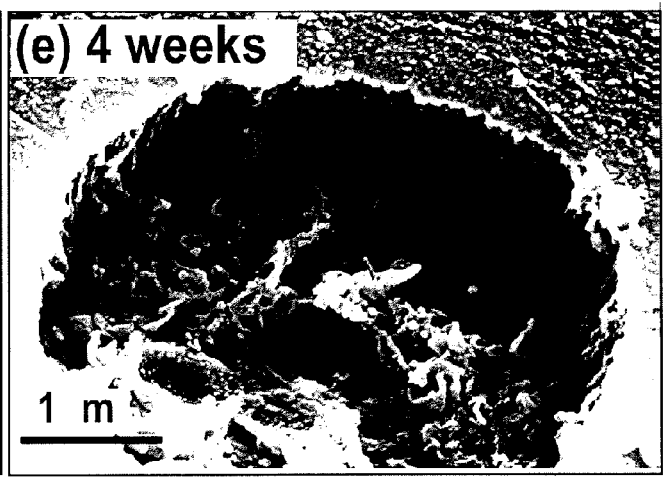
FIG. 19D     FIG. 19E

3-DIMENSIONAL PARYLENE SCAFFOLD CAGE

CROSS-REFERENCES TO RELATED APPLICATIONS

This application is a Continuation-in-Part application of U.S. patent application Ser. No. 13/355,426, filed Jan. 20, 2012, which application claims the benefit of U.S. Application Ser. No. 61/566,965, filed Dec. 5, 2011. This application also claims the benefit of U.S. Provisional Patent Application No. 61/586,276, filed Jan. 13, 2012, wherein all of the foregoing applications are hereby incorporated by reference in their entireties for all purposes.

BACKGROUND

Age-related macular degeneration (AMD) is the leading cause of blindness among patients over 65 years of age in industrialized nations (C. J. Lee et al., *Biomaterials,* 27:1670-1678 (2006); J. T. Lu et al., *Biomaterials,* 28:1486-1494 (2007)). Evidence has been shown that AMD is usually associated with the dysfunction of retinal pigment epithelial (RPE) cells and the degeneration of underlying Bruch's membrane. Human Bruch's membrane is a thin (2-4 μm in thickness), compact layer of collagen fibers located between the retina and vascular choroid, and it is semipermeable to allow the transports of nutrients and other macromolecules from the underlying blood vessels to retina. Directly on the Bruch's membrane is a monolayer of hexagonally shaped RPE cells that interface with photoreceptors. On the apical surface of polarized RPE cells, microvilli are developed for the interdigitation of RPE cells with the photoreceptor outer segments. One theory postulates that, in AMD, RPE cells stop degrading the waste products from photoreceptors properly, leading to the accumulation of wastes in Bruch's membrane (C. J. Lee et al., *Biomaterials,* 27:1670-1678 (2006); J. T. Lu et al., *Biomaterials,* 28:1486-1494 (2007)). As a result, Bruch's membrane may become clogged and thickened, and its composition can change with lower permeability to nutrients, which can cause the dysfunction of RPE cells, the loss of photoreceptors, and ultimately severe vision loss.

Direct transplantation of healthy RPE cells to replace the diseased ones was once considered as a potential treatment. However, it was proven later to be difficult because sometimes the transplanted RPE cells failed to adhere and form a monolayer on the diseased Bruch's membrane (C. J. Lee et al., *Biomaterials,* 27:1670-1678 (2006 T. Lu et al., *Biomaterials,* 28:1486-1494 (2007)).

What is needed in the art are new ways to transplant retinal pigment epithelial cells as well as other cells. More etticatious treatments for age-related macular degeneration and other diseases are also needed. The present invention satisfies these and other needs.

BRIEF SUMMARY OF THE INVENTION

Generally, devices, systems, and methods for manufacturing a semipermeable parylene C membrane are disclosed. Parylene C—which has been found to be permeable to proteins in serum at ultrathin thicknesses (e.g., 0.01 μm to 5 μm thick)—is manufactured into a membrane having a smooth front side and tiny hills and valleys on the back side, such that it has a variable thickness. The hills and valleys, which can be stepwise-edged like a city skyline or histogram, can be manufactured using lithographic techniques.

One way of manufacturing such a membrane is to etch a relatively thick parylene film with tiny, through-hole perforations, lay it on a smooth substrate, and deposit an ultrathin layer of parylene over the perforated thick layer. The resulting parylene membrane is then peeled off of the substrate. The side of the membrane that was against the substrate is smooth, as the ultrathin layer of parylene covers the openings of the perforations. The opposite side of the membrane remains rough with hills and valleys because the ultrathin layer of deposited parylene was not enough material to fill in the etched perforations.

Embodiments of the present invention relate to a synthetic semipermeable membrane apparatus. The apparatus includes a membrane having a smooth front side, a back side, and spatially interspersed thin and thick regions between the smooth front side and the back side, the thin regions being a predetermined thickness of parylene, the predetermined thickness selected from a thickness between 0.01 μm to 5 μm, such as 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 μm. The thick regions comprise parylene or another material and are at least 2 times thicker than the predetermined thickness of the thin regions, and the interspersion of the thin and thick regions occur in a random or patterned array with an average feature size of about 1 μm to 10 μm, such as 1, 2, 3, 4, 5, 6, 7, 8, 9, or 10 μm.

Some embodiments relate to a synthetic semipermeable membrane apparatus, including a supporting film having a plurality of through perforations extending from a first side to an opposing, second side of the supporting film, and a 0.01- to 5-μm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 μm) thin parylene layer covering an opening of each perforation of the supporting film.

Some embodiments relate to a process for fabricating a synthetic semipermeable membrane. The process includes providing a supporting film having through perforations extending from a first side to an opposing, second side of the supporting film, laying the first side of the supporting film against a smooth substrate surface, depositing a 0.01- to 5-μm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 μm) thin parylene layer over the supporting film sufficient to cover a bottom of each perforation of the supporting film to form a membrane with a smooth first side, and removing the membrane from the smooth substrate surface.

Some embodiments relate to a method of using a synthetic semipermeable membrane, the method including providing a membrane that has a supporting film having a plurality of through perforations extending from a first side to an opposing, second side of the supporting film and a 0.01- to 5-μm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8 and 5.0 μm) thin parylene layer covering an opening of each perforation of the supporting film wherein the covered openings of the perforations are even with a surface of the first side of the supporting film, thereby forming a substantially smooth surface on the first side. The method further includes diffusing molecules through the membrane.

In other embodiments, the present invention provides a three-dimensional (3-D) scaffold or cage comprising a synthetic semipermeable membrane. In order to hinder or prevent cell migration, the present invention provides a three-dimensional (3-D) scaffold (i.e. a cage) by assembling a parylene 'fishnet' cover onto a mesh-supported submicron parylene bottom or membrane so that the cells are constrained inside the cage. Advantageously, the 3-D cage satisfies a medical need. First, the cage's bottom is as permeable as Bruch's membrane, which allow nutrients transportation to nourish the cells inside. Secondly, the cage is mechanically robust, which allows for bending and stretching and handling during surgery. Moreover, the cage's top fishnet blocks cell migration, but allow microvilli or other cellular processes and structures to connect to outside the cage. Finally, under such constraints, cells are able to proliferate inside with normal morphology.

Reference to the remaining portions of the specification, including the drawings and claims, will realize other features and advantages of the present invention. Further features and advantages of the present invention, as well as the structure and operation of various embodiments of the present invention, are described in detail below with respect o the accompanying drawings.

BRIEF DESCRIPTION OF THE DRAWINGS

FIG. 4A illustrates depositing an initial thick parylene layer in a manufacturing process for a semipermeable membrane in accordance with an embodiment.

FIG. 4B illustrates a metal and photoresist application step in the manufacturing process of FIG. 4A.

FIG. 4C illustrates a photolithographic exposure step in the manufacturing process of FIG. 4A.

FIG. 4D illustrates an etching step in the manufacturing process of FIG. 4A.

FIG. 4E illustrates a peeling of the thick layer step in the manufacturing process of FIG. 4A.

FIG. 4F illustrates an attachment of the thick layer to another substrate in the manufacturing process of FIG. 4A.

FIG. 4G illustrates deposition of an ultrathin layer of parylene in the manufacturing process of FIG. 4A.

FIG. 4H illustrates the completed membrane removed from the second substrate in the manufacturing process of FIG. 4A.

FIG. 4I illustrates the membrane being used to grow a monolayer of cells after the manufacturing process of FIG. 4A.

FIG. 13A-F illustrates a manufacturing process of the top portion of a 3-D cage of the present invention.

FIG. 13G-H illustrates scanning electron micrographs of an embodiment of the present invention.

FIG. 19A-E illustrates one embodiment of in vitro culture data of the present invention.

DETAILED DESCRIPTION OF THE INVENTION

I. Embodiments

Figure 1A:
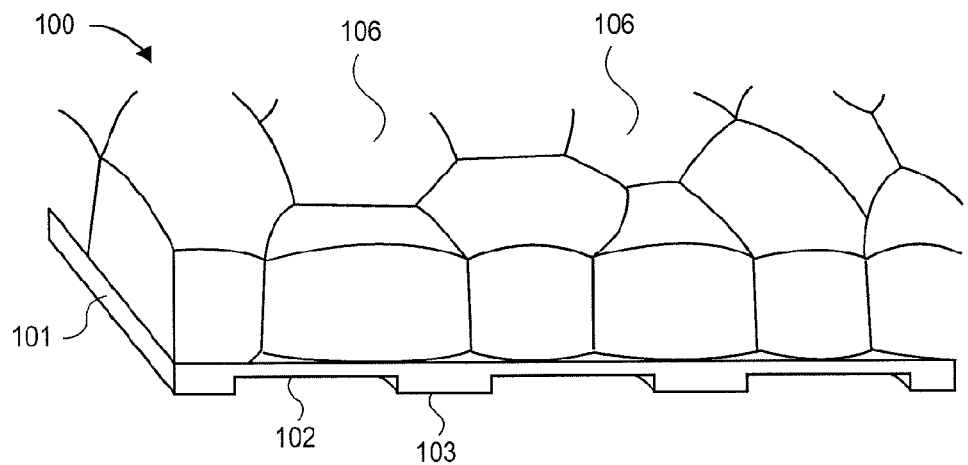
FIG. 1A is an oblique, cut-away top view of a semipermeable membrane growing a monolayer of cells in accordance with an embodiment.

Generally, devices, systems, and methods for manufacturing a semipermeable parylene C membrane and a 3-dimensional cage incorporating the membrane are disclosed. A membrane with ultrathin (e.g., 0.01 µm to 5 µm thick) parylene regions is arranged to have a smooth side and a spatially variable thickness. The smooth side can be used to grow a monolayer of cells, while the bumps or undulations on the second side prevent cell growth on the second side. The ultrathin portions of the parylene are permeable to protein-sized molecules but impermeable to cells, which are on the order of 4 µm (for tiny photoreceptor rod and cone cells of the retina) to greater than 20 µm. The thicker portions of the membrane, which are interspersed with the thin portions, make the membrane stronger, less prone to folding or undulating, and generally easier to handle for surgeons.

Prior art porous membranes have been found to have disadvantages. First, the fabrication of small holes (i.e., <0.1 µm) is difficult to perform reliably. Therefore, in some applications where the cut-off selective size of the particles has to be smaller than 0.1 µm, porous membranes usually are not capable for biological applications. Second, when used in on-membrane cell culture applications, the porous topology may disturb the adherence and morphology of biological cells. The nooks and crannies of the pores present a non-smooth, variable surface, which is suboptimal for the growth of even cell monolayers. This can make the in vitro cultured cells very different from cells growing in their in vivo natural environment.

Materials that are naturally semipermeable are known, such as collagen and polydimethylsiloxane (PDMS). However, the surfaces of these semipermeable materials are often sponge-like. They are often not biocompatible, so they are not proper for implantation applications. Furthermore, they are difficult to reliably pattern into desired shapes and designs.

Parylene (including all the parylene derivatives such as parylene N, C, D, HT, AM, A, etc.) has been shown to be a superior biocompatible material, but it is usually used as a protective coating to prevent harmful large molecules from going through it. The inventors have not only determined how to use parylene as a permeable material, but they have also performed an in-depth study of the permeability of ultrathin parylene C to optimize the "thickness design" of parylene semi-permeable membranes. It has been found that parylene is permeable below some thicknesses, and the thinner the parylene, the more permeable it is. Furthermore, it is proposed that parylenes with thicknesses from 0.01 µm to 5 µm (or 0.01, 0.1, 0.2, 0.3, 0.4, 0.5, 0.6, 0.7, 0.8, 0.9, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, and 4.8 µm) can readily be used as semipermeable membranes in medical applications when coupled with thicker frames and supporting films.

Technical advantages of some of the embodiments are many. The smooth surface of the front side of a membrane is advantageous for cell growth than rough or spongy surfaces. The thin parylene areas allow nutrients and cell waste to pass through the membrane, while the thick areas give mechanical support and rigidity so that the membrane is less prone to tearing, folding, undulating, etc. during implantation. The thickness of the ultrathin parylene can be scaled for growing any cell type in a monolayer for implantation in the body. For example, retinal pigment epithelium (RPE) can be grown in a monolayer on the membrane. Cartilage trabeculae, heart muscle, and other cells can be grown in a monolayer as well. Besides facilitating in vitro perfusion cell culture, semipermeable parylene-C membrane also has use in the in vivo replacement of a Bruch's membrane in the eye for age-related macular degeneration. Bruch's membrane allows the passage of molecules with MW below 75 kDa.

An embodiment may be able to replace impaired human semipermeable tissue membranes anywhere in the human body, not just the Bruch's membrane. For example, the human lens capsule and collagen film can use parylene C membranes thinner than 0.30 µm.

As a proof of design, ultrathin parylene C membranes with thicknesses ranging from 0.15 µm to 0.80 µm have been experimentally verified. At least four different thicknesses (i.e., 0.15 µm, 0.30 µm, 0.50 µm, and 0.80 µm) of parylene C membranes manufactured on perforated support films were subject to diffusion studies using fluorescein isothiocyanate (FITC)-dextran molecules of different molecular weights (MWs) at body temperature (37° C.; 98.6° F.). A diffusion coefficients for each of five molecules (i.e. 10 kDa, 40 kDa, 70 kDa, 125 kDa, and 250 kDa) was obtained by fitting concentration-time curves into the equation:

$$C_2 = \frac{C_0 V_1}{V\left(1 - \exp\left(-\frac{Dt}{\tau h}\right)\right)} \quad \text{Eqn. 1}$$

where $$\tau = \frac{\left(V_1 + \frac{A_{eff} h}{2}\right)\left(V_2 + \frac{A_{eff} h}{2}\right)}{A_{eff} V} \quad \text{Eqn. 2}$$

where $C_0$ is the initial concentration on a first side of the membrane, $C_2$ is the concentration on the second side of the membrane (where $C_2$ at the start of each experiment is 0), $V_1$ and $V_2$ are the volumes of liquid on the respective sides of the membrane and $V=V_1+V_2$ (i.e., the total volume), h is the thickness of the ultrathin regions of the membrane (i.e., 0.15 µm, 0.30 µm, 0.50 µm, and 0.80 µm), and $A_{eff}$ is the effective area of the ultrathin portion of the membrane.

Because the membrane's thick regions were 20-µm diameter holes with a center-to-center spacing of 30 µm, $A_{eff}$ for all the tested membranes is:

$$A_{eff} = \frac{\pi (0.10 \ \mu m)^2}{0.30 \ \mu m \times 0.30 \ \mu m} \quad \text{Eqn. 3}$$

After obtaining the diffusion coefficients, the theoretical MW exclusion limit was then calculated for each thickness of film by extrapolating the linear relationship between the diffusion coefficients an the natural log of MW (i.e., ln(MW)) to a diffusion coefficient of zero. The results of this calculation are tabled in Table 1. Also tabled are respective exclusion radiuses (and diameters), calculated from the MWs of the FITC-dextran molecules.

TABLE 1

| Thickness (µm) | Exclusion MW (kDa) | Exclusion radius (µm) | Exclusion diameter (µm) |
|---|---|---|---|
| 0.15 | 1,302 | 0.02560 | 0.05120 |
| 0.30 | 1,008 | 0.02262 | 0.04524 |
| 0.50 | 291 | 0.01239 | 0.02478 |
| 0.80 | 71 | 0.0625 | 0.01250 |

Determining exclusion diameters of certain thicknesses of parylene is only part of the solution. While an ultrathin material may work in a laboratory, it may not be suitable in real-world situations.

Working with extremely thin parylene is difficult. To facilitate and strengthen the mechanical bending, stretching, and handling of ultrathin parylene, a thick supporting substrate design is disclosed. The supporting substrate is preferably thicker (e.g., 1-30 µm) than the ultrathin layers, such as two times as thick as the ultrathin layer. It can have various geometries, such as a mesh, net, pore, etc. geometry.

Further, a new substrate having an ultrathin parylene membrane with its back filled with some extremely permeable materials, such as silicone or hydrogels, is proposed for certain applications.

U.S. Patent Application Publication No. 2011/0236461 A1 to Coffey et al., published Sep. 29, 2011 (hereinafter "Coffey"), describes a polymer membrane for supporting the growth of retinal pigmented epithelial (RPE) cells in the human eye. Coffey discloses membrane pores between 0.2 µm and 0.5 µm in diameter (Coffey paragraph [0009]). The pore diameters in Coffey are substantially larger than exclusion diameters present in parylene C at the 0.01- to 5-µm thicknesses presented in this application (e.g., 0.0512 µm diameter; see Table 1). Furthermore, Coffey teaches that its membrane is preferably made from a hydrophilic polymer, such as polyester (see, e.g., Coffey paragraphs [0024] and [0043]), where parylene is characteristically hydrophobic.

The figures will be used to further describe aspects of the application.

Figure 1B:
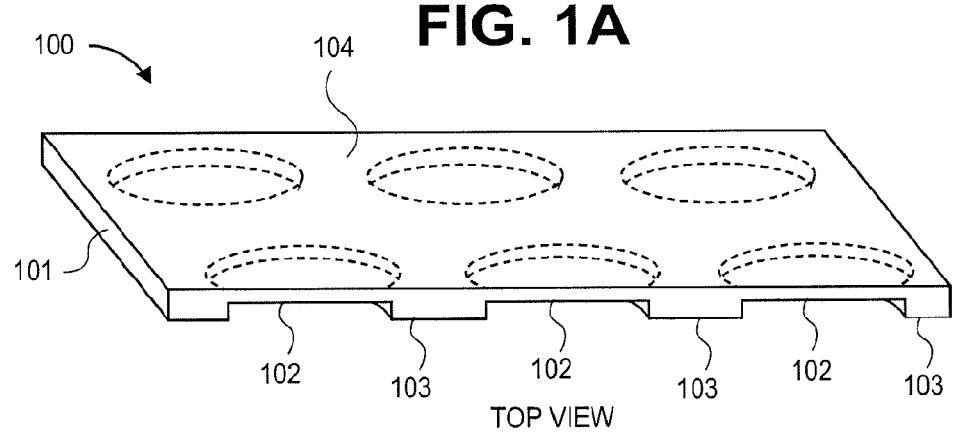
FIG. 1B is an oblique, cut-away top view of the semipermeable membrane of FIG. 1A without the cells.
Figure 1C:
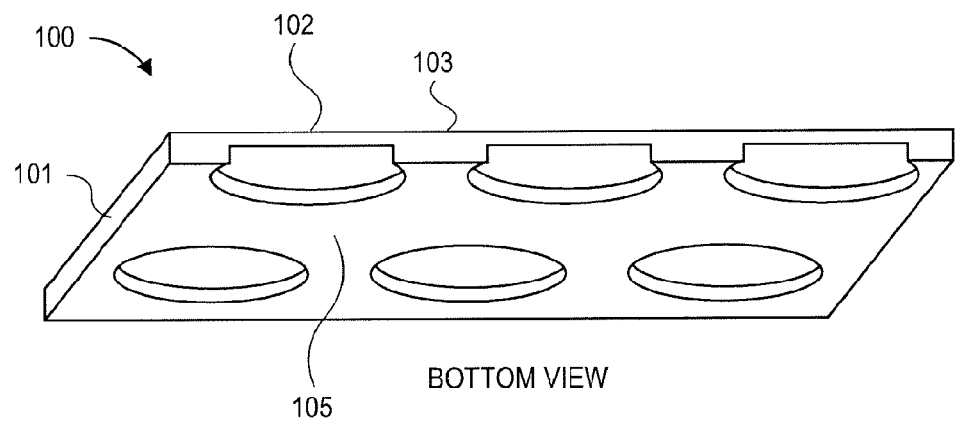
FIG. 1C is an oblique, cut-away bottom view of the semipermeable membrane of FIG. 1B.

FIGS. 1A-1C are oblique, cut-away views of a semipermeable membrane in accordance with an embodiment. FIG.

1A shows cells 106 growing on top of the membrane, while FIG. 1B omits the cells. FIG. 1C shows a bottom view of the membrane.

Biocompatible membrane system 100 includes membrane 101 having a front, top side 104 and a back, bottom side 105. Orientation terms of "front," "top," "back," "bottom," etc, are for the convenience of the reader and are not limiting as to absolute orientation. Front side 104 is smooth, having no salient protrusions or recesses that inhibit the natural formation of cells growing as a monolayer. Back side 105 is relatively rough, inhibiting or reducing the growth of cells.

Membrane 101 includes thin regions 102 interspersed with thick regions 103. In this embodiment, thick regions 103 are substantially contiguous with one another, and thin regions 102 comprise cylindrical recesses in the membrane. Thin regions 102 are interspersed in a regular, grid-like patterned array on membrane 101. In some embodiments, a random array, as opposed to one with a recognizable pattern, can be interspersed on the membrane. Embodiments having a combination of patterned and random arrays are also contemplated.

On front side 104, thin regions 102 flow cleanly with thick regions 103 to form a smooth surface as shown in FIG. 1B. On back side 105, thin regions 102 abruptly change to the plateaus of thick regions 103, forming a rough surface.

The thin regions are of a predetermined thickness, predetermined based on a permeability desired. For example, to allow proteins having a molecular weight of 70 kDa or smaller to flow through while inhibiting molecules having a molecular weight of over 100 kDa, the thickness of the thin regions can be engineered to be 0.80 µm thick (see Table 1).

The thick regions can be 2, 3, 4, 5, or 10 (and gradations in between) or more times thicker than the thin sections. Their increased thickness allows the entire membrane to be more easily handled. In the exemplary embodiment, thick regions 103 are 3 times the thickness of thin regions 102. In certain applications, thicknesses of more than 6 µm may be unwieldy. In some other cases, thick region thicknesses between 1 µm and 30 µm (such as 2, 3, 4, 5, 6, 7, 8, 9, 10, 11, 12, 13, 14, 15, 16, 17, 18, 19, 20, 21, 22, 23, 24, 25, 26, 27, 28, and 29 µm) thick can be used.

In other embodiments, the thin regions can be substantially contiguous with one another, with the thick regions comprising protrusions from the back side of the membrane. That is, instead of a bunch of holes as shown in FIG. 1C, there can be a bunch of mounds or other protrusions from an otherwise thin membrane.

"Substantially contiguous" regions include those that are flat with respect to each other without barriers or whose barriers are less than 10, 15, 20, or 25% of the respective regions' widths or as otherwise known in the art.

Figure 2A:
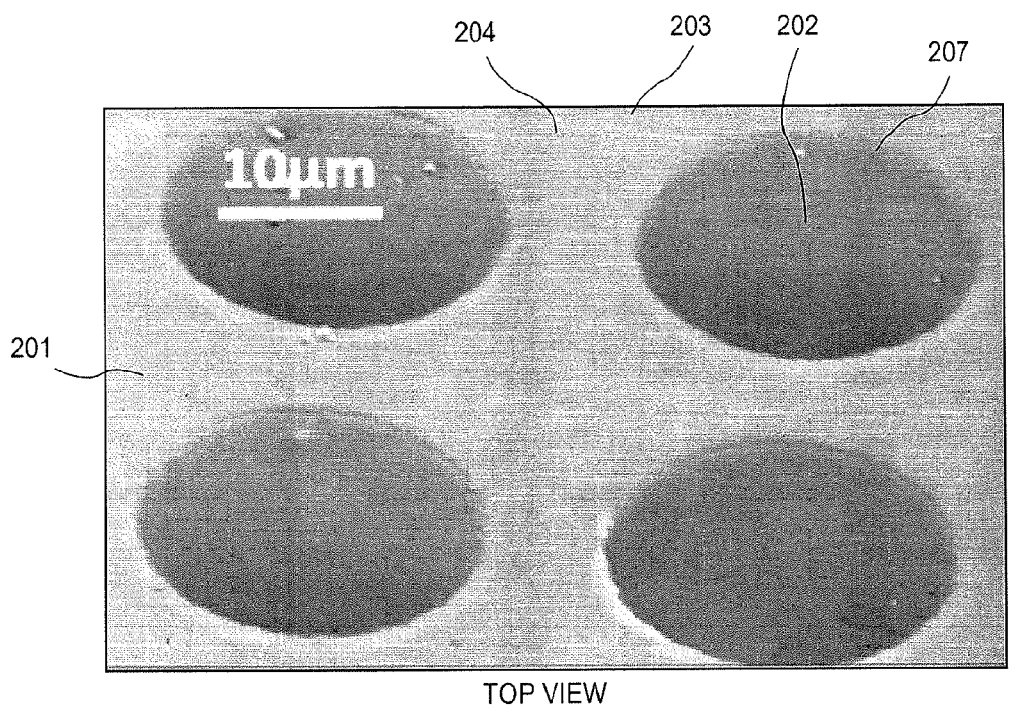
FIG. 2A is a scanning electron microscope (SEM) image of a top side of a semipermeable membrane manufactured in accordance with an embodiment.
Figure 2B:
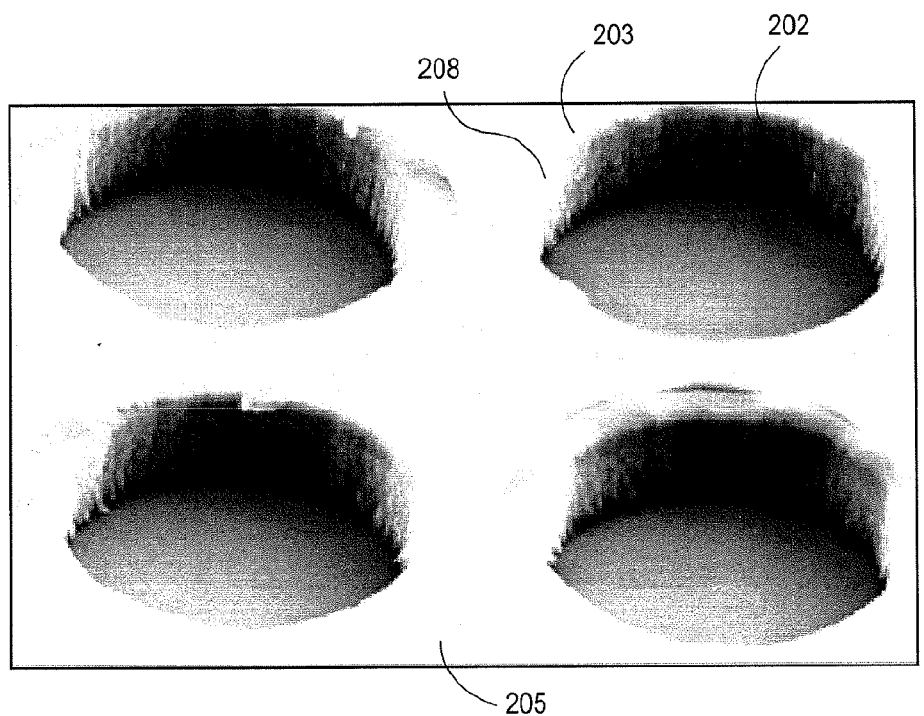
FIG. 2B is a scanning electron microscope (SEM) image of a bottom side of the semipermeable membrane of FIG. 2A.

FIGS. 2A-2B are scanning electron microscope (SEM) images of top and bottom sides of a semipermeable membrane manufactured in accordance with an embodiment.

In FIG. 2A, thin regions 202 of membrane 201 are almost transparent as seen from top side 204. They exhibit a drum-head like appearance, stretching over openings 207 in thick regions 203. Thicknesses of between 0.1 µm to 10 µm are considered to be a good range for many biological cells, allowing diffusion of proteins in serum to flow through the membrane. Thicknesses between 0.15 µm to 0.8 µm have been studied in depth. Thick regions of 3 µm to 4 µm thick allow a surgeon to manipulate the membrane with less chance of tearing, fold back, or undulation.

In FIG. 2B, recess 208 appears as a hole in thick region 203, bottoming out with thin region 202. The walls of recess 208 have been coated with an ultrathin layer of parylene to approximately the same thickness as the thin regions 202 as a result of a chemical vapor deposition (CVD) process described below.

In certain instances, membrane 201 can be at least one side or face of a cage-like scaffold. For example, in one embodiment, the present invention provides an implantable cage-like apparatus for culturing cells. The cage-like structure can be implanted into a human or an animal. The cage-like apparatus comprises a three-dimensional apparatus or cube having six faces including a top face or portion, a bottom face or portion and four side faces or portions, wherein the cage-like apparatus has eight vertices. Each side may be the same or different.

In one embodiment, membrane 201 is the bottom portion or face of a cage-like apparatus. In one preferred aspect, the smooth front side of membrane 201 is within the cage, wherein the smooth side promotes cell growth. The back side 205, which is relatively rough, inhibits or reduces the growth of cells. This portion is on the outside of the cage. In one aspect, the cage comprises a membrane, the membrane having a smooth front side, a back side, and spatially interspersed thin and thick regions between the smooth front side and the back side. The thin regions have a predetermined thickness of parylene, the predetermined thickness are selected from a thickness of between 0.01 µm to 5 µm, and the thick regions comprise parylene or another material and are at least 2 times thicker than the predetermined thickness of the thin regions. The interspersion of the thin and thick regions occur in a random or a patterned array with an average feature size of about 1 µm to 30 µm.

Figure 3:
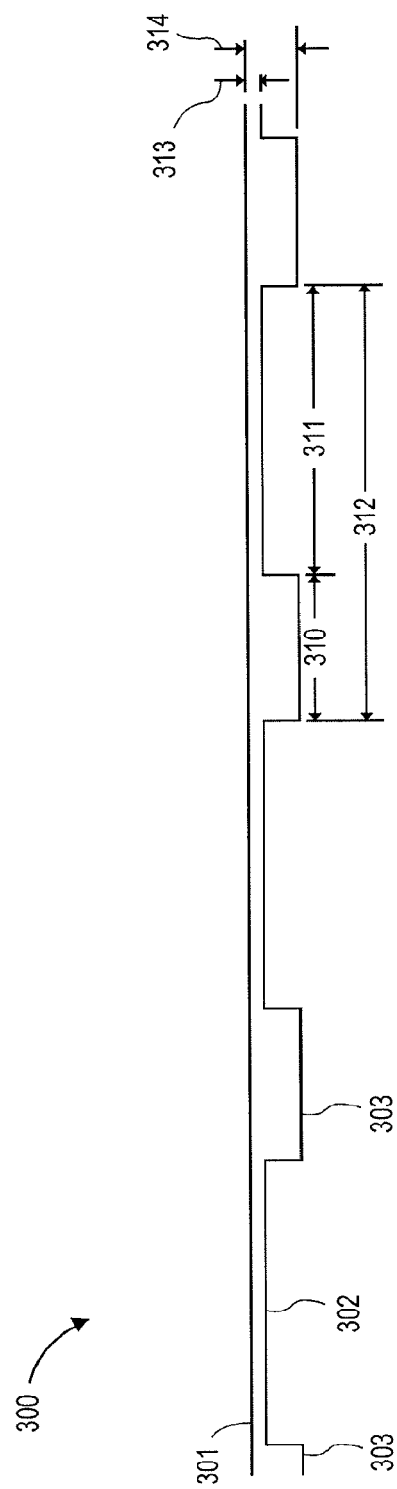
FIG. 3 is a side, elevation view of a semipermeable membrane in accordance with an embodiment.

FIG. 3 is a side, elevation view of a semipermeable membrane in accordance with an embodiment. Substrate 300 includes membrane 301 with thick regions 303 interspersed with repeating thin regions 302. Average feature size 310 of the plateaus between the repeating thin regions is about 10 µm (e.g., 7, 8, 9, 10, 11, or 12 µm). The thin regions are about 20 µm (17, 18, 19, 20, 21, or 22 µm) in diameter. The average, edge-to-edge (or center-to-center) pitch 312 is 30 µm (e.g., 26, 27, 28, 29, 30, 31, 32 µm). Thin region thickness 313 is 1 µm, while thick region thickness 314 is 3-4 µm. This spacing has been found to inhibit or reduce growth of cells that are about 20 µm in length.

FIGS. 4A-4H illustrate a manufacturing process for a semipermeable membrane in accordance with an embodiment.

As shown in FIG. 4A, an 8-µm thick supporting film 422 of parylene C is deposited on a cleaned, HMDS- (hexamethyldisilazane- or hexamethyldisiloxane-) treated silicon substrate 421. As shown in FIG. 4B, aluminum 423 is deposited on the parylene C supporting film 422 as an etching mask, followed by photoresist layer 424. As shown in FIG. 4C, photoresist layer 424 is illuminated in a random or patterned array using light 427. The photoresist becomes insoluble in regions 425 and soluble in regions 426. Soluble photoresist 426 is then washed away. As shown in FIG. 4D, wet-etching and reactive-ion etching (RIE) is used to etch 20 µm-diameter holes through supporting film 422 down to silicon substrate 421, to create array 428.

As shown in FIG. 4E, the now-perforated parylene layer 422 is removed from silicon substrate 421. As shown in FIG. 4F, perforated parylene layer 422 is attached to a different HDMS-treated silicon substrate 431. As shown in FIG. 4G, ultrathin parylene C film 429 (e.g., 0.15 µm to 0.80 µm thick) is then deposited on supporting film 422. The chemical vapor deposition (CVD) process results in a thin layer of parylene coating the walls as well as the bottom of the recesses. As shown in FIG. 4H, the completed membrane is peeled off, reversed and treated with $O_2$ plasma. The entire membrane, including both its thick and thin sections, is parylene, such as parylene C.

Manufactured membrane 401 has front side 404 (on the bottom in the figure) and back side 405 (on the top in the figure). Thin sections 402 are interlaced with thick sections 403 in pattern 428.

FIG. 4I illustrates membrane 401 being used to grow a monolayer of cells. The membrane has been rotated so that front side 404 faces up and back side 405 faces down. Cells 406 grow on smooth, front side 404 of membrane 401. Cells can be grown on the membrane in any orientation.

Figure 5:
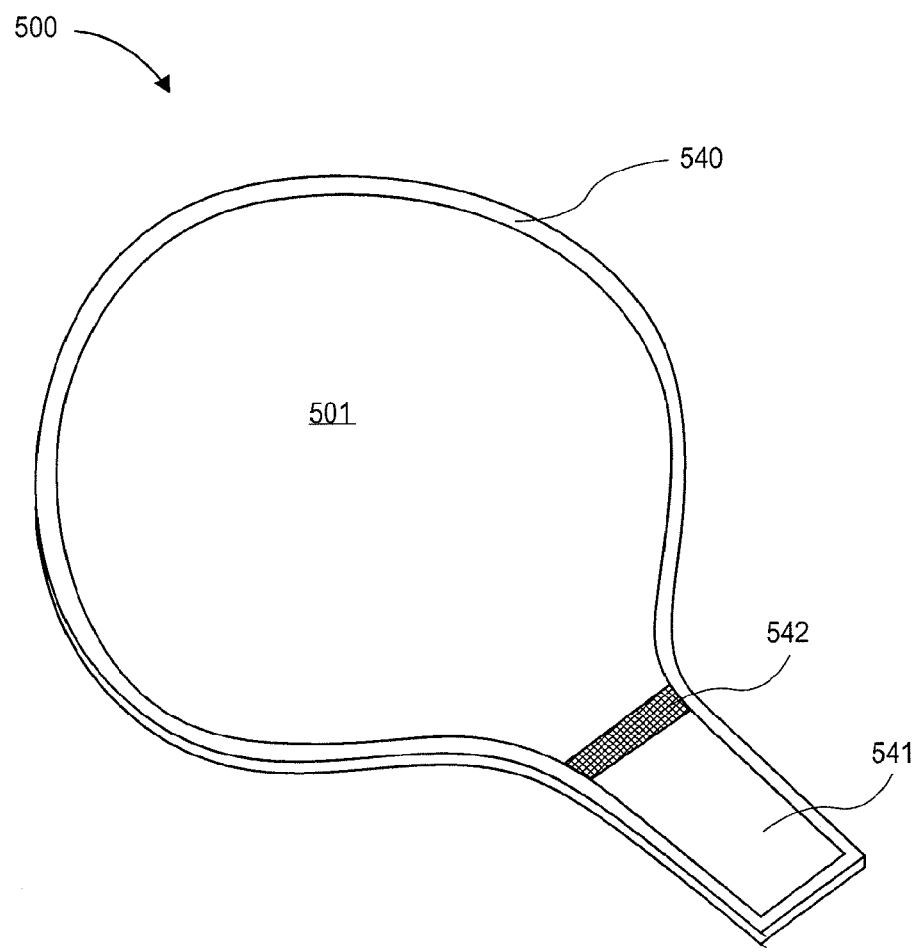
FIG. 5 illustrates an implantable membrane in accordance with an embodiment.

FIG. 5 illustrates an implantable membrane in accordance with an embodiment. Implantable membrane system 500 includes membrane 501 having tiny interlaced regions of ultrathin and thick biocompatible parylene. Frame 540 surrounds membrane 501 with a thick, relatively sharp edge that prevents or retards cells from migrating from a front, smooth side of the membrane to the back. Not only does frame 540 prevent or retard cells from migrating, but the relatively pointy and sharp edges of the rough side of the membrane prevents cells from gaining a foothold on the back side of the membrane. In this way, a surgeon can maximize the healthy monolayer growth of cells on one side of the membrane while minimizing undesirable cells on the back of the monolayer. This can be important in some applications, such as replacing the RPE behind the retina in the eye.

Tab 541 allows a surgeon's forceps or tool to hold the membrane, with cut-off section 542, or as otherwise described in U.S. patent application Ser. No. 61/481,037, filed Apr. 29, 2011.

Figure 6:
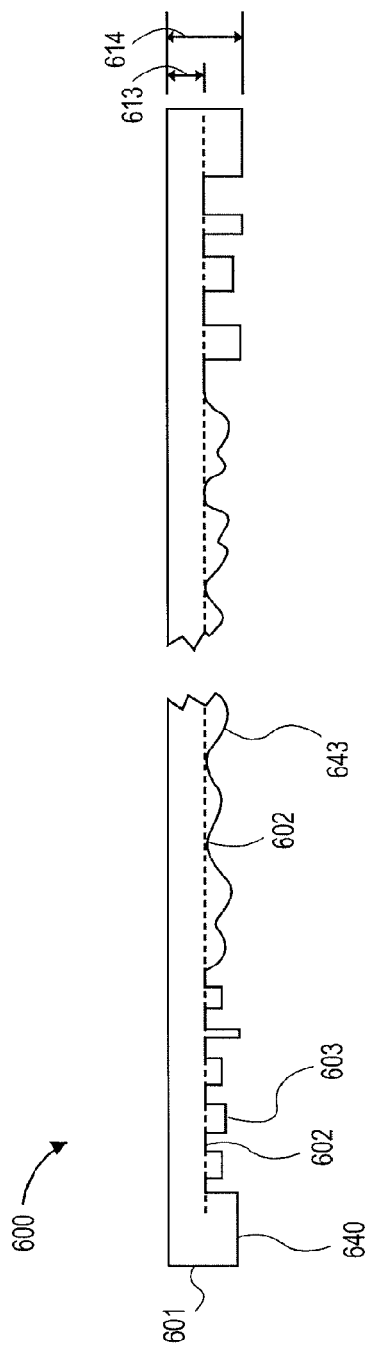
FIG. 6 is a side, elevation view of a semipermeable membrane with sharp and soft features in accordance with an embodiment.

FIG. 6 is a side, elevation view of a semipermeable membrane with sharp and soft features in accordance with an embodiment. Membrane system 600 includes membrane 601 with thin regions 602 of predetermined thickness 613.

Near circumference ring 640, membrane 601 includes thick regions 603 that have rectangular cross sections. Farther away from circumference ring 640, near the center of membrane 601, are thick regions 643 having rounded cross sections. Thick regions 603 have relatively sharp features with respect to thick regions 643, and thick regions 643 have relatively smooth features in comparison with thick regions 603.

Having relatively sharp regions near the circumference can retard or prevent cells that do happen to migrating around the edges of the membrane from growing on the membrane. Near the center, where there is less of a chance of cells migrating, the hills and valleys of the thick and thin regions can be smooth so that the membrane is better accepted during implantation and more compatible with the body.

Figure 7:
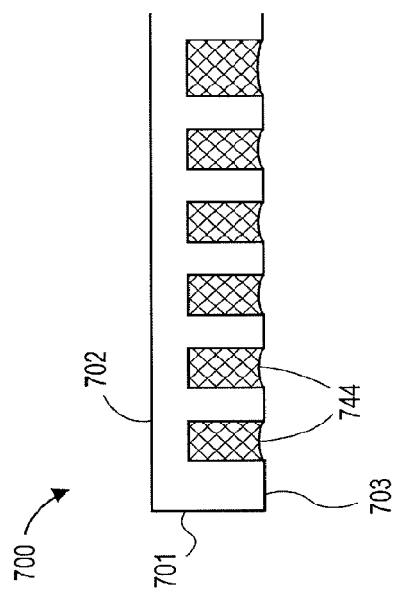
FIG. 7 is a side, elevation view of a semipermeable membrane with backfilled depressions in accordance with an embodiment.

FIG. 7 is a side, elevation view of a semipermeable membrane with backfilled depressions in accordance with an embodiment. In membrane device 700, membrane 701 has thin regions 702 and thick regions 703. Depressions on the bottom side where the thin regions exist are filled with a biocompatible, porous hydrogel 744, which smoothes out the hills and valleys of the back side. This can be used in situations where a smooth surface for cell growth is desired on the back side of the membrane. Cells can grow on both sides of the membrane, as both sides have relatively smooth surfaces compared with the size of the cells to be grown.

Figure 8:
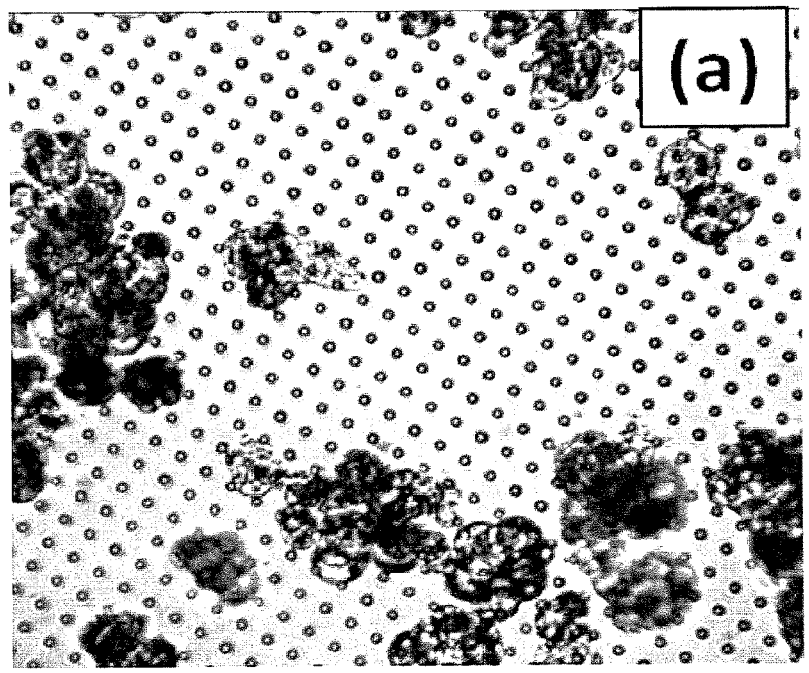
FIG. 8 is an image of cell growth on a porous membrane of the prior art.

FIG. 8 is an image of cell growth on a porous membrane of the prior art, showing H9-RPE (retinal pigment epithelial) cells cultured on a porous parylene-C membrane with oxygen plasma treatment. Note the clumpy adherence of cells, which is undesirable.

Figure 9:
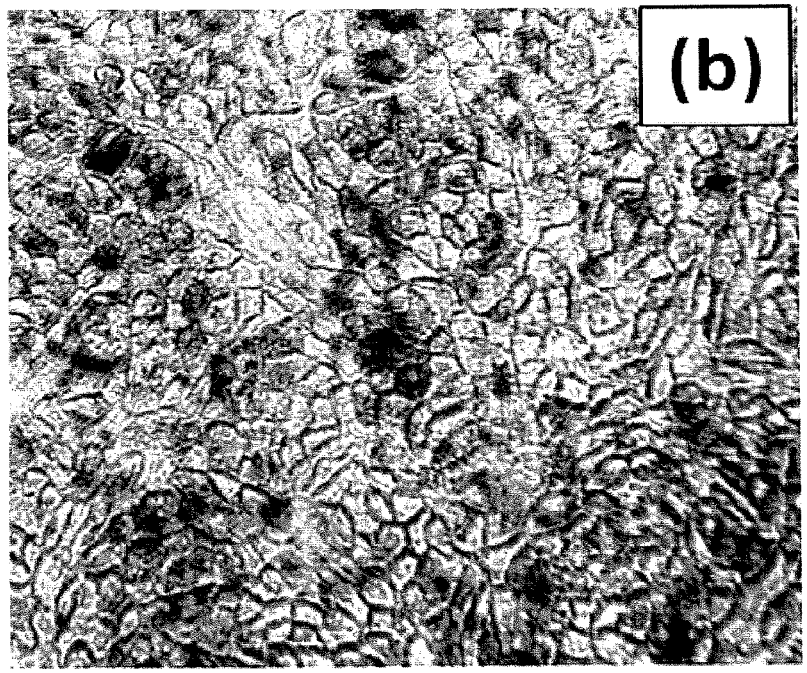
FIG. 9 is an image of cell growth on a semipermeable membrane in accordance with an embodiment.

FIG. 9 is an image of cell growth on a semipermeable membrane in accordance with an embodiment. The cell morphology is very different from that in FIG. 8. In FIG. 9, the cells grow in a relatively flat monolayer, having access to plenty of nutrients through the membrane and able to discharge cell waste through the membrane. The cells proliferated well, became confluent after ten days of culture, and showed clear signs of polarization. The cells also have desirable hexagonal boundaries.

Figure 10:
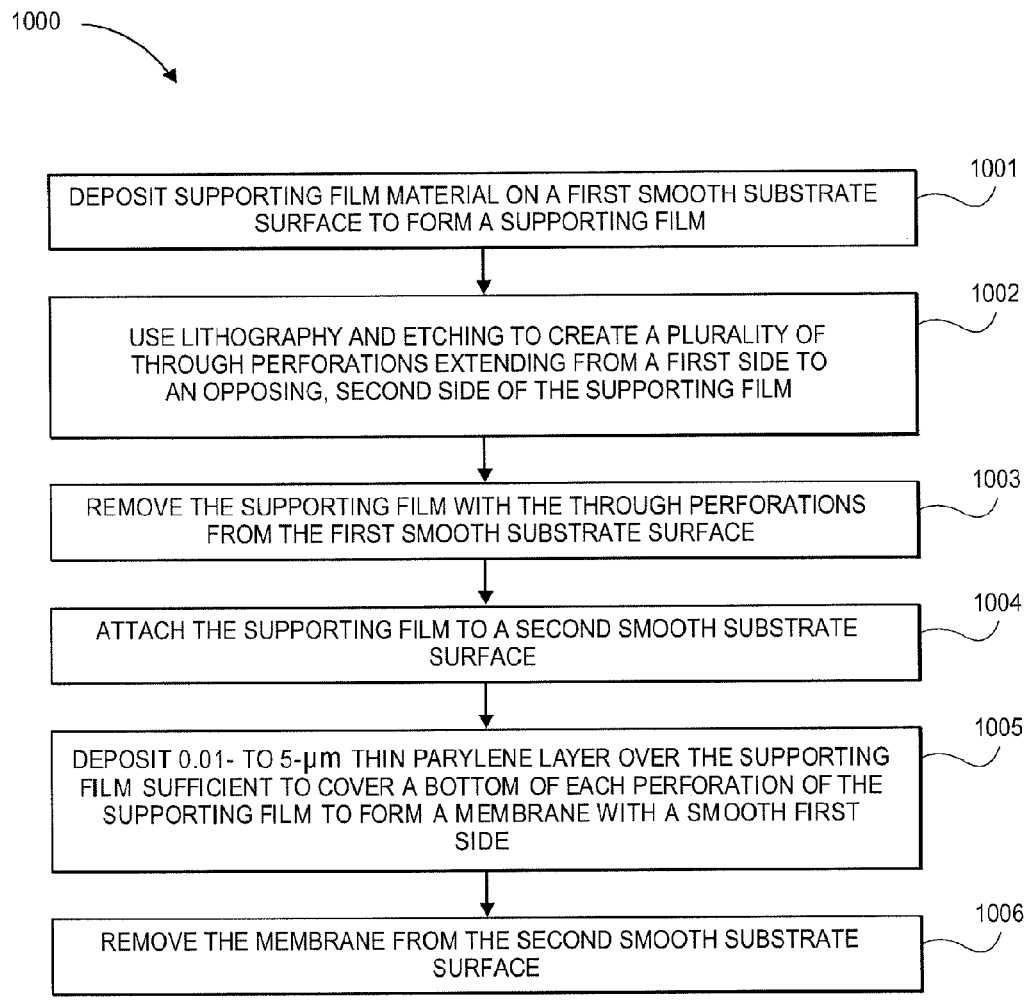
FIG. 10 is a flowchart illustrating a process in accordance with an embodiment.

FIG. 10 is a flowchart illustrating process 1000 in accordance with an embodiment. In operation 1001, a supporting film material is deposited on a first smooth substrate surface to form a supporting film. In operation 1002, lithography and etching are used to create a plurality of through perforations extending from a first side to an opposing, second side of the supporting film. In operation 1003, the supporting film with the through perforations is removed from the first smooth substrate surface. In operation 1004, the supporting film with the through perforations is attached to a second smooth substrate surface. In operation 1005, a 0.01- to 5-μm thin parylene layer is deposited over the supporting film sufficient to cover a bottom of each perforation of the supporting film to form a membrane with a smooth first side. In operation 1006, the membrane is removed from the second smooth substrate surface and readied for implantation.

Figure 11:
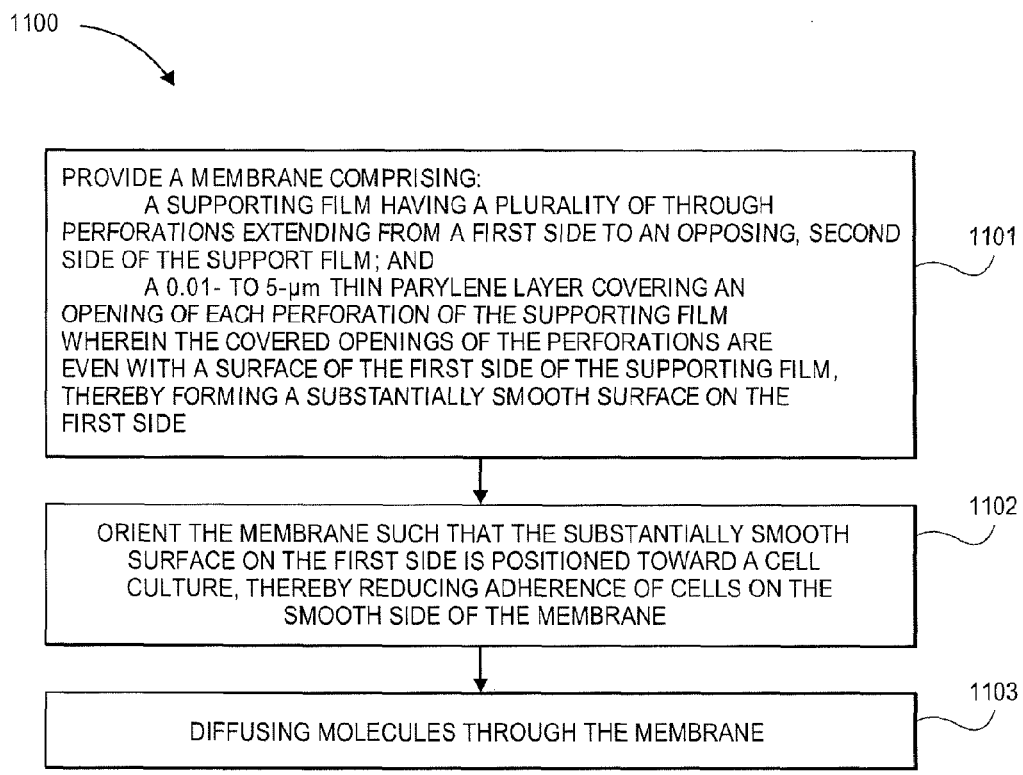
FIG. 11 is a flowchart illustrating a process in accordance with an embodiment.

FIG. 11 is a flowchart illustrating process 1100 in accordance with an embodiment. In operation 1101, a membrane is provided, the membrane comprising: a supporting film having a plurality of through perforations extending from a first side to an opposing second side of the supporting film; and a 0.01- to 5-μm thin parylene layer covering an opening of each perforation of the supporting film wherein the covered openings of the perforations are even with a surface of the first side of the supporting film, thereby forming a substantially smooth surface on the first side. In operation 1102, the membrane is oriented such that the substantially smooth surface on the first side is positioned toward a cell culture, thereby reducing adherence of cells on the smooth side of the membrane. In operation 1103, molecules are diffused through the membrane.

In certain aspects, it is desirable to strengthen the membrane or bottom portion by creating a cage-like structure or a mesh. This embodiment increases the mechanical strength over the membrane alone.

Figure 12C:
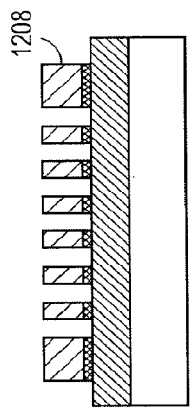
FIG. 12A-H illustrates a manufacturing process of the bottom portion of a 3-D cage of the present invention.
Figure 12F:
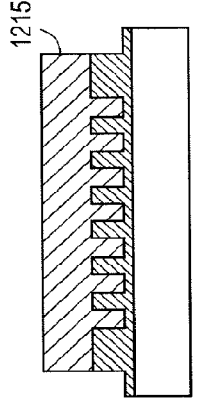
Figure 12B:
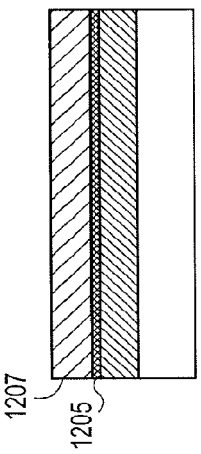
Figure 12E:
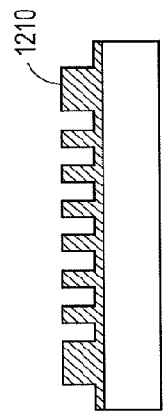
Figure 12H:
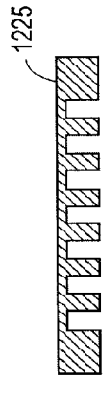
Figure 12A:
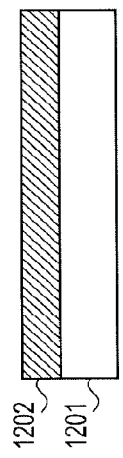

FIGS. 12A-H show one embodiment of the fabrication process of the bottom portion of a 3-dimensional cage apparatus of the present invention. In one aspect, the fabrication process starts with a parylene-C deposition on hexamethyldisilazane (HMDS) treated silicon. As is shown in FIG. 12A, the first step of the fabrication of the cage-like apparatus is the deposition of parylene-C 1202 on a HMDS treated silicon 1201. The parylene C preferably has a thickness of about 1 μm to 10 μm such as about 6 μm. The parylene-C depositions can be performed with a parylene coating equipment at temperature settings of 180° C. and 690° C. for the vaporizer and furnace, respectively. In certain aspects, the set-point of chamber pressure during deposition is about 35 mTorr. The HMDS coating is used to reduce the adhesion between parylene-C and silicon.

Figure 12D:
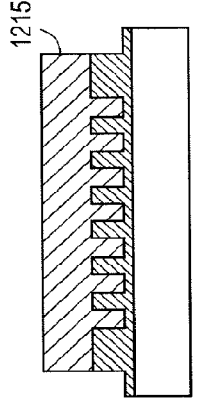

Next, aluminum or another suitable material is then deposited as the parylene-C etching mask. FIG. 12B shows the deposition of an aluminum coating 1205, which is thereafter followed by a photoresist spin-coating 1207. Following lithography, wet etching of aluminum, and reactive ion etching (RIE) with oxygen plasma, parylene-C is patterned with circular through holes as a mesh frame. FIG. 12C shows the lithography step and then wet-etching of aluminum to form a mask 1208 for parylene-C etching. FIG. 12D shows the mesh frame etched 1209 by reactive ion etching (RIE). After RIE, diluted hydrofluoric acid (HF) is used to clean the residues inside the holes.

Figure 12G:
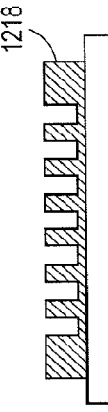

Following residue cleaning, a submicron parylene-C film 1210 (e.g., 0.15-0.80 µm) is then deposited on the mesh frame. In FIG. 12E, the deposition of a 0.30 µm parylene-C layer is shown. A second lithography step is done to cover the whole device with photoresist. In FIG. 12F, the mesh supported submicron parylene C membrane (MSPM) is covered with photoresist 1215 after a second lithography. The contour of the device is then formed by etching away ultrathin parylene-C in undesirable regions. FIG. 12G shows the contour 1218 of the MSPM being formed by RIE. Finally, the whole membrane is peeled off and flipped over. Both sides of the membrane are treated with low power oxygen plasma (power: 50 W, chamber pressure: 200 mTorr, duration: 1 min) for better cell adherence. FIG. 12H shows the membrane or bottom portion 1225 of the cage having been peeled off and flipped over.

Figures 12I, 12J, 12K:
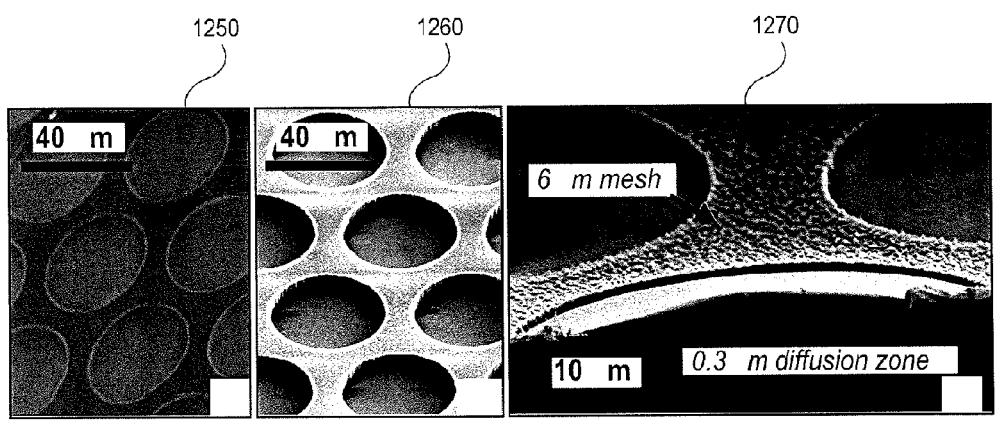
FIG. 12I-K illustrates scanning electron micrographs of an embodiment of the present invention.

FIG. 12I-K show SEM pictures of the front side 1250, backside 1260 and cross section 1270, respectively, of the membrane or bottom portion. The circular regions of the submicron membrane are diffusion zones. The front side was treated with low power (50 W, 200 mTorr, 1 min) oxygen plasma to facilitate cell adhesion.

In another embodiment, the top portion of a 3-D cage is fabricated as is shown in FIGS. 13A-F. For example, as is shown in FIG. 13A, a 1 µm-thick parylene layer 1301 is deposited onto silicone 1305. FIG. 13B shows the parylene being patterned into a fish-net like structure 1301 with through holes. As is shown in FIG. 13C, the porous region is then covered with sacrificial photoresist 1307. Next, FIG. 13D shows a 6 µm-thick parylene coat thereafter being deposited 1315. FIG. 13E shows that after patterning, only the edge of the second parylene layer remains 1315. FIG. 13F shows that the top is finally released and flipped over. In one aspect, the top cover is a 1 µm-thick fishnet 1327 with 4 µm-diameter holes. A skilled artisan will understand that the 1 µm-thick fishnet is exemplary. In certain aspects, the thickness is between 0.1 µm to 3 µm such as 0.1, 0.2, 0.3, 0.4, 0.5, 0.6, 0.7, 0.8, 0.9, 1.0, 1.2, 1.4, 1.6. 1.8, 2.0. 2.2, 2.4, 2.6, 2.8, or 3.0 µm. The 4 µm diameter is also exemplary. This diameter can vary between 1.0 µm to 6 µm such as 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, and 6.0 µm. In one aspect, the edge of the cover is about 6 µm thick, and is used as a spacer when the top portion is placed onto and thereafter affixed to the bottom substrate. The spacer is between 1 µm to 20 µm thick such as 1, 2, 3, 4, 5, 6, 7, 8, 9, 10, 11, 12, 13, 14, 15, 16, 17, 18, 19 or 20 µm thick. In certain aspects, the posts are between 5 µm to 10 µm thick.

In certain aspects, as is shown in FIG. 13F, the top portion resembles a bridge-like structure, with two posts 1325A, 1325B (the spacers), that support a fish-net top-portion 1327. FIG. 13G is a view looking down at the fish-net portion 1327 of the bridge. Although the preferred openings in the fish-net are shown as circles, any geometry is suitable. These geometries include, squares, triangles, rectangles, circles and the like. The fish-net surface allows cells to make physical contact with their microenvironment, while still be contained.

In certain aspects, the present invention provides a bridge-like structure made of parylene, the bridge-like structure comprising: a first supporting post; a second supporting post; and a fish-net surface or face connecting the first supporting post and the second supporting post.

After fabrication of a top portion and a bottom portion, a 3-D cage is assembled. As illustrated in Example 4, the top or "cover" portion is assembled onto a bottom using a method to affix the sections. Suitable fixation means include an adhesive, a cement, fusion, welding and the like. Suitable biocompatible adhesives or cements include, for example, Matrigel or bone cements such as polymethyl methacrylate or other suitable cements. Those of skill in the art will know of other fixation means suitable for use in the present invention.

After assembly, the cage allows containment of cells. Unlike simply injecting cells into a portion of a human body or animal where the cells are free to roam promiscuously, the inventive cage contains cells within the implanted section and within the confines of the cage. In addition to containing the implanted cells, the cage also allows for explanting the cells and the 3-D structure as well.

In one embodiment, the present invention provides a method for retarding or preventing cell migration from the site of implantation. Quite advantageously, after implantation the apparatus of the present invention can be removed (explanted) and thereby remove the implanted cells as well.

Figures 14A, 14B, 14C:
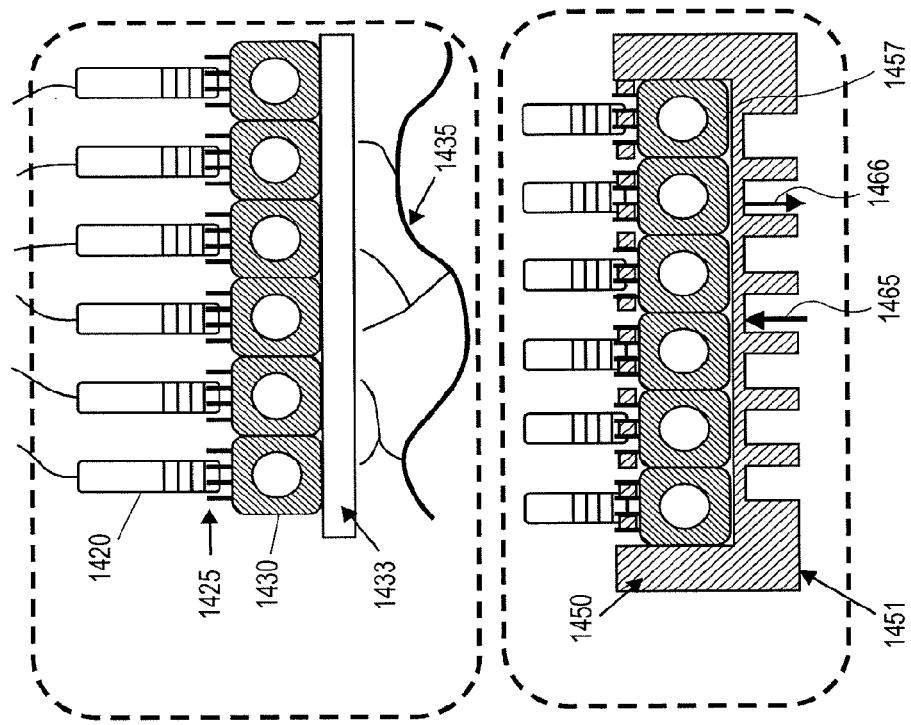
FIG. 14A-C illustrates one embodiment of the apparatus of the present invention.

FIGS. 14A-C show one embodiment of the apparatus of the present invention. FIG. 14A is an illustration of the human eye. The parts as illustrated include the retina 1401; the choroid 1402; the sclera 1404; the retinal pigment epithelial (RPE) 1405; Bruch's membrane 1407 and the lens 1409.

FIG. 14B shows an enlarged view of a section of the eye. In this enlarged section, 6 photoreceptors are shown 1420. Below the photoreceptors are microvilli 1425, which reside above the RPE cells 1430. The RPE cells appear above Bruch's membrane 1433. Bruch's membrane is nourished by the choroid capillaries 1435.

Turning now to FIG. 14C, to prevent or retard cell migration, a 3D RPE scaffold (i.e., a cage) is implanted. By assembling a parylene 'fishnet' onto a mesh-supported submicron parylene bottom 1451, the cells 1457 are constrained inside the cage. Advantageously, the cage satisfies several requirements. First, the cage's bottom 1451 is similarly permeable to Bruch's membrane. This permeability allows nutrients transportation to nourish the cells inside. For example, the cells have access to nutrients 1465 and waste exchange 1466 to outside the bottom of the cage.

Second, the bottom 1451 is mechanically robust, which allows for bending and stretching during implantation and surgery. Moreover, the cage's top fishnet 1450 is able to block or substantially retard cell migration, but still allow for example, the microvilli to connect to the outside photoreceptors. Finally, under such constraints, cells 1457 are able to proliferate inside the cage-like apparatus with normal morphology and develop microvilli on the apical surface.

In certain other embodiments, the present invention provides a synthetic Bruch's membrane comprising the implantable cage-like apparatus as described herein. In addition, the present invention provides an area of missing or degenerated cartilage comprising the implantable cage-like apparatus as described herein. Moreover, the present invention provides an artificial pancreas for the treatment of diabetes comprising the implantable cage-like apparatus as described herein.

II. Examples

Example 1 illustrates the permeability of the implantable cage-like apparatus is comparable to a Bruch's membrane.

To measure the permeability of the bottom substrate, a blind-well diffusion experiment was performed. A mesh-supported submicron parylene-C with 0.3 μm submicron membrane was clamped in-between two blind well chambers (Neuro Probe, Inc.). FITC-dextran molecules (Sigma-Aldrich Co.) with various molecular weights (MW) were initiated in the bottom chamber. The top chamber was initially filled with phosphate buffered saline (PBS).

By monitoring the fluorescence intensity in the top chamber, the diffusion coefficients of dextran molecules were calculated using a previously described method (B. Lu, Z. Liu and Y. C. Tai, "Ultrathin parylene-C semipermeable membranes for biomedical applications", Proc. of MEMS 2011, Cancun, Mexico, Jan. 23-27, 2011, pp. 505-508). The permeability of 0.3 μm parylene-C was compared with the healthy human Bruch's membranes, in terms of the molecular flux at the same concentration gradient. The permeability data of Bruch's membrane were obtained from healthy donors aged 9-87 years (A. A. Hussain, C. Starita, A. Hodgetts, J. Marshall, "Macromolecular diffusion characteristics of ageing human Bruch's membrane: Implications for age-related macular degeneration (AMD)", Exp. Eye. Res., vol. 90, pp. 703-710, 2010).

Figure 15A:
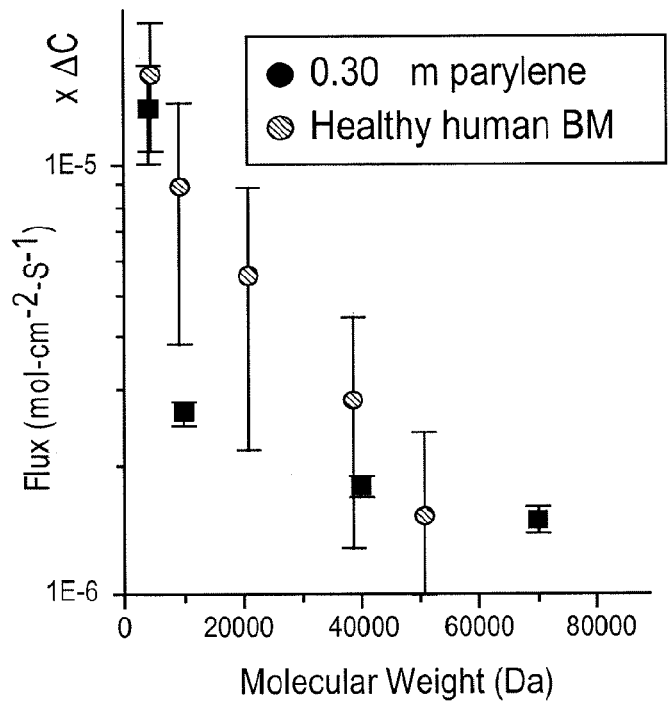
FIG. 15A-B illustrates permeability data of an embodiment of the present invention.

FIG. 15A illustrates the permeability evaluation, wherein the measurement of diffusion flux of FITC-dextran molecule is compared in 0.3 μm parylene-C versus healthy human Bruch's membranes. In fact, the data shows that 0.3 μm parylene-C has comparable permeability with Bruch's membrane.

To further verify that the parylene-C membrane supports sufficient nutrients to nourish the RPE cells, perfusion cell viability tests were also carried out. The mesh-supported submicron parylene-C membranes (with 0.3 μm submicron parylene-C) were clamped in-between two blind-wells, with the cultured cells exposed to the contents of the top chambers. Either culture medium or PBS was filled in the chambers and the cells were further cultured for 12 hrs. (H9-RPE) or 3 hrs. (ARPE-19) under three different conditions (medium-medium, PBS-medium and PBS-PBS). The viability of RPEs was then determined by Calcein-AM/Propidium Iodide (PI) (Invitrogen) staining.

For the PBS-medium (P-M) condition, since sufficient nutrients could diffuse from the bottom to upper wells, the viability was comparable to the medium-medium (M-M) condition (positive control). However, due to the depletion of nutrients, the viability was considerably lower for the PBS-PBS (P-P) condition (negative control).

Figure 15B:
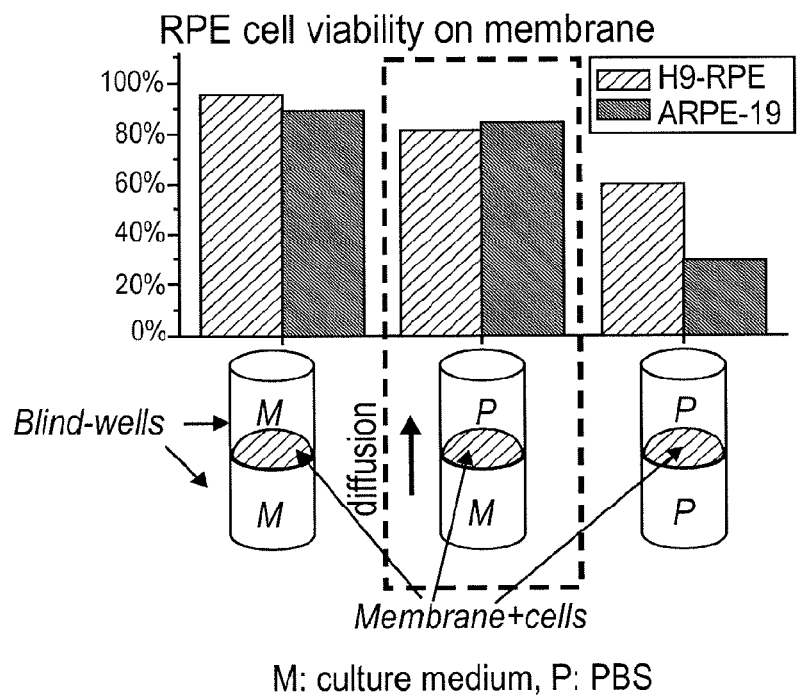

FIG. 15B shows the perfusion cultures of two types of RPE cells (H9 RPE and ARPE-19). 0.3 μm parylene allowed sufficient diffusion of nutrients from the bottom culture medium well to the top PBS well to maintain the cell viability on membrane as the middle cell viability is comparable to the left hand side membrane viability.

Example 2 illustrates the mechanical strength of the implantable apparatus.

Example 2 illustrates membrane deflection experiments to evaluate the mechanical properties of the parylene membranes, in terms of their yielding pressures and breakdown pressures. The yielding pressure was defined as the minimum pressure that could create wrinkles and irreversible deformation. The breakdown pressure was recorded at the moment the membrane broke. Compared to the large uniform 0.3 μm parylene film, it was observed that the mesh-supported structure greatly improved the mechanical strength of the entire membrane (Table 2).

TABLE 2

| Membrane types (overall diameter is 1.8 mm) | Ratio of thin part | Yielding pressure | Breaking pressure |
| --- | --- | --- | --- |
| Uniform 0.3 μm parylene | 100% | 1.50 psi | 3.32 psi |
| Mesh-supported 0.3 μm parylene | 53% | 4.88 psi | 19.94 psi |

Figure 16B:
FIG. 16A-B illustrates the mechanical strength of an embodiment of the present invention.
Figure 16A:
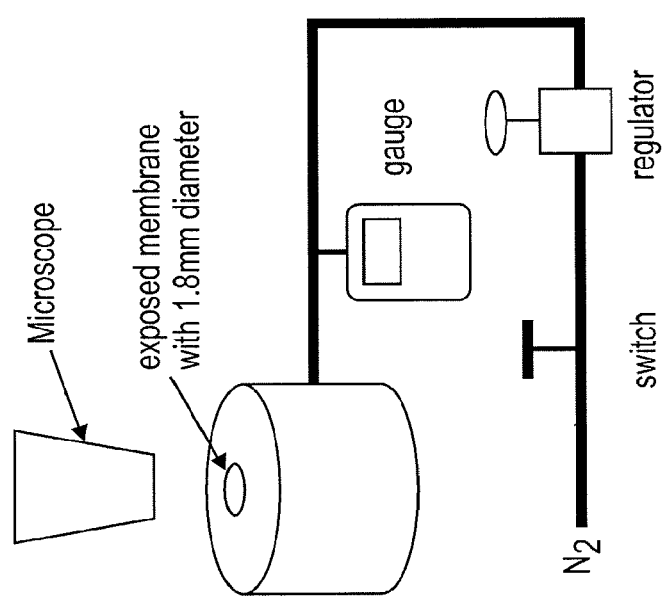

FIG. 16A shows the membrane mechanical property testing experimental set-up. As shown therein, the membrane pressure deflection testing set-up includes a microscope; an exposed membrane with 1.8 mm diameter; a nitrogen source; a switch; a regulator and a gauge.

FIG. 16B shows the SEM picture of a broken mesh-supported membrane. The submicron membrane regions can be stretched a lot before breakdown. For this reason, the bottom was designed with packed 0.3 μm-thick circular parylene membranes in hexagonal arrangement. As a result, not a single broken membrane has been found during handling and culturing experiments. In fact, mesh-supported submicron parylene was stretched a lot before broken at 19.94 psi, exhibiting good mechanical strength.

Example 3 illustrates a cell migration experiment of the implantable apparatus.

Once sealed inside a cage, RPE cells need to develop microvilli to connect to photoreceptors. Therefore, the cage's top cover can have a fishnet-like structure, exposing the microvilli, but blocking the migration of the whole cell. In one embodiment, the gap between the top and bottom was 6 μm, determined by the height of adhering polarized cells.

Figure 17:
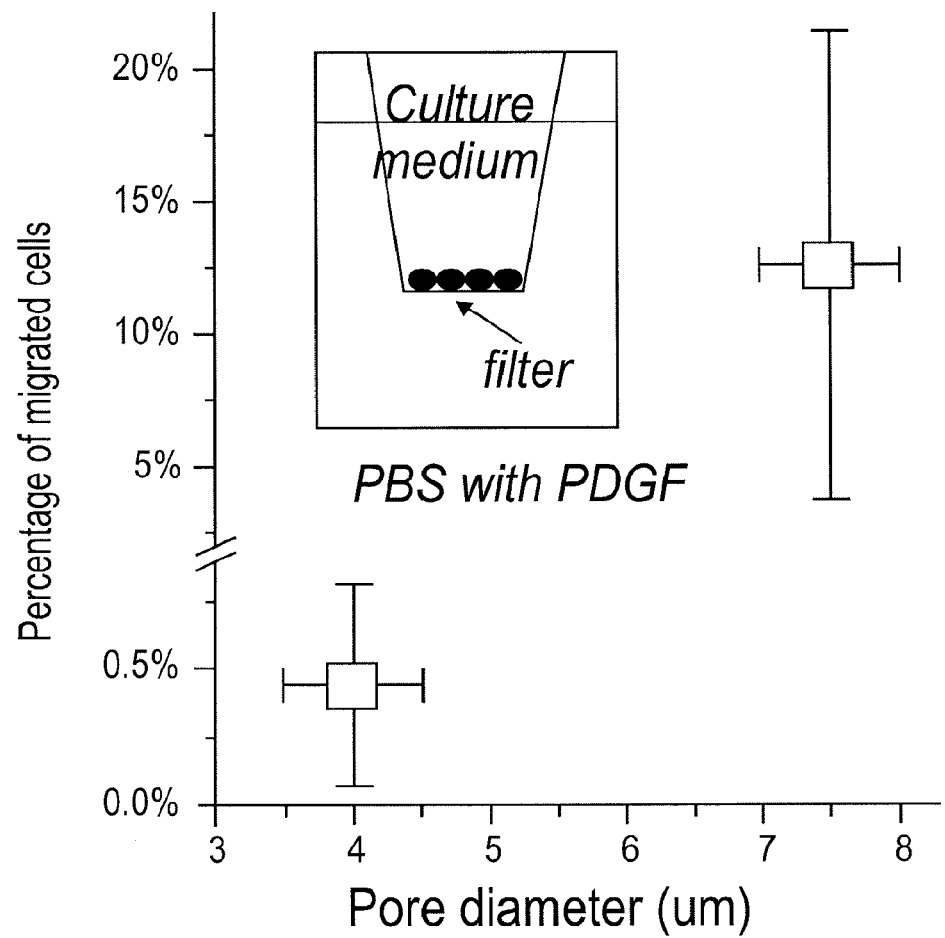
FIG. 17 illustrates the results of one embodiment of a cell migration experiment of the present invention.

To determine the size of opening, cell migration experiments were carried out with the transwell setup. Porous parylene membranes with 8 μm-diameter and 4 μm-diameter holes were fabricated using the method described in (B. Lu, T. Xu, S. Zheng, A. Goldkorn and Y. C. Tai, "Parylene membrane slot filter for the capture, analysis and culture of viable circulating tumor cells", Proc. of MEMS 2010, Hong Kong, China, Jan. 24-28, 2010, pp. 935-938). Platelet-derived growth factor (PDGF) was added to the bottom well, which was a stimulus of cell migration. Holes with 8 μm-diameter are widely used as a semi-barrier to evaluate RPE cell migration (C. M. Chan, J. H. Huang, H. S. Chiang, W. B. Wu, H. H. Lin, J. Y. Hong and C. F. Hung, "Effects of (−)-epigallocatechin gallate on RPE cell migration and adhesion," Mol. Vis., vol. 16, pp. 586-595, 2010). FIG. 17 shows that the percentage of migrated cells through 4 μm-diameter holes was significantly reduced to 0.5%, which is considered as a good barrier. The inset shows the transwell setup.

Example 4 illustrates assembling of the implantable apparatus.

Figure 18A:
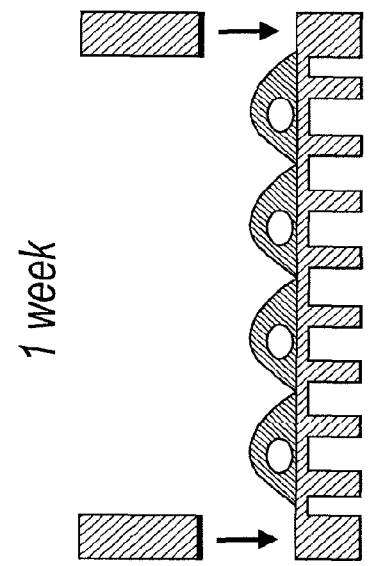
FIG. 18A-D illustrates one embodiment of assembling an apparatus of the present invention.
Figure 18C:
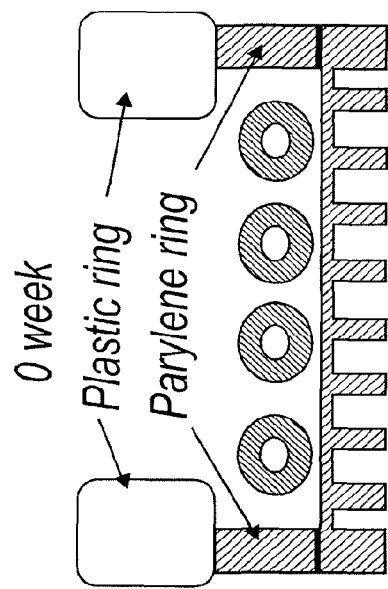
Figure 18B:
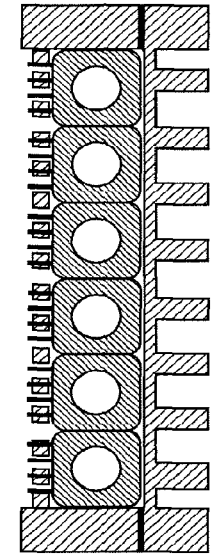
Figure 18D:
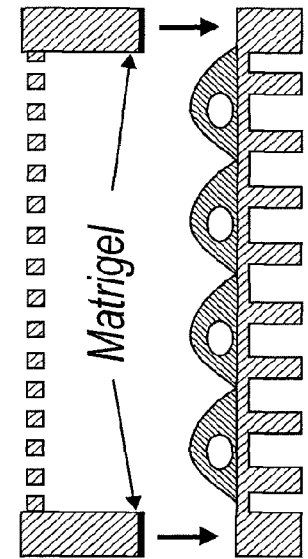

In operation for in vitro culture experiments, a parylene ring was first placed on the bottom substrate before cell seeding to protect the assembling region. FIG. 18A show at the beginning, a parylene ring and a plastic ring are used. FIG. 18B shows that after the cells evenly spread on the substrate and get confluent, the parylene ring was removed to expose the non-cell region. FIG. 18C shows that the top or "cover" was assembled to the non-cell region on the bottom using Matrigel (BD Biosciences) as 'biological glue'. Undiluted Matrigel was used here because it was sticky enough to glue two parylene surfaces together in either wet or dry environment, especially after incubation at 37° C. FIG. 18D shows the culturing process was continued until the cells were polarized with microvilli exposed through the top cover openings.

Example 5 illustrates the use of the implantable apparatus in cell culturing.

FIGS. 19A-E show the in vitro RPE cell culture results. As is shown in FIG. 19A, one week after seeding, the cells got confluent on the bottom substrate. Then the top cover was placed on the bottom. FIGS. 19B and 19C show that after four weeks, cells started to become polarized and pigmented inside the cage. Cells were fixed and stained with anti-ZO-1 antibody (Millipore) to visualize the morphology and tight junctions among the cells. FIG. 19D indicates that the cells were in a monolayer with hexagonal shapes and intercellular tight junctions, which are good signs of typical epithelial-like morphology. After the fixation, dehydration and conductive coating of the samples, the cage was observed using SEM. FIG. 19D shows that the polarized cell was constrained inside the cage. The microvilli were clearly visible on the apical surface of the cell and exposed through the cover's opening. Once implanted, cells cultured inside the cage can form interdigitation with photoreceptors through these exposed microvilli.

The invention has been described with reference to various specific and illustrative embodiments. However, it should be understood that many variations and modifications may be made while remaining within the spirit and scope of the following claims.

What is claimed is:

1. A method of manufacturing an implantable membrane, the method comprising:
   depositing a film material on a first substrate surface to form a supporting film;
   creating a plurality of perforations on the supporting film;
   removing the supporting film from the first substrate surface;
   attaching the supporting film to a second substrate surface;
   depositing a parylene layer over the supporting film wherein the parylene layer is sufficient to cover a bottom of each perforation on the supporting film to form a membrane with a smooth first side;
   orienting the membrane such that the smooth first side is positioned toward a cell culture; and
   diffusing molecules through the membrane.

2. The method of manufacturing of claim 1, wherein the first substrate surface is smooth.

3. The method of manufacturing of claim 1, wherein etching is used to create the plurality of perforations.

4. The method of manufacturing of claim 1, wherein lithography is used to create the plurality of perforations.

5. The method of manufacturing of claim 1, wherein the plurality of perforations extend from a first side of the first supporting film to an opposing, second side of the supporting film.

6. The method of manufacturing of claim 1, wherein the second substrate surface is smooth.

7. The method of manufacturing of claim 1, wherein the parylene layer has a thickness between 0.01 µm to 5 µm.

8. The method of manufacturing of claim 1, wherein the orientation of the membrane is configured to reduce adherence of cells on the smooth side of the membrane.

9. The method of manufacturing of claim 1, further comprising the mechanical strength of the membrane by attaching a cage-like structure or mesh.

10. A method of manufacturing a structure for providing mechanical strength to an implantable membrane, the method comprising
    depositing a first layer of parylene-C on silicone;
    depositing a first material on the first layer of parylene-C;
    applying a second coating over the first material;
    lithographing and wet-etching the first material and the second coating to form a mask for parylene-C etching;
    etching the first layer of parylene-C to form a mesh frame;
    depositing a second layer of parylene-C on the mesh frame;
    lithographing the mesh frame and depositing a layer of photo-resist on the mesh frame;
    etching away undesirable regions in the mesh frame; and
    removing the mesh frame from the silicone.

11. The method of manufacturing of claim 10, wherein the first layer of parylene C has a thickness of about 1 µm to 10 µm.

12. The method of manufacturing of claim 10, wherein the first layer of parylene-C has a thickness of about 6 µm.

13. The method of manufacturing of claim 10, wherein the deposition of the first layer of parylene-C is performed with a vaporizer at a temperature 180° C.

14. The method of manufacturing of claim 10, wherein the deposition of the first layer of parylene-C is performed with a furnace at a temperature of 690° C.

15. The method of manufacturing of claim 10, wherein the deposition of the first layer of parylene-C is performed at a chamber pressure of 35 mTorr.

16. The method of manufacturing of claim 10, wherein the silicone is treated with hexamethyldisilazane.

17. The method of manufacturing of claim 10, wherein the first material is aluminum.

18. The method of manufacturing of claim 10, wherein the second coating is a photoresist spin-coating.

19. The method of manufacturing of claim 10, wherein the etching of the first layer of parylene-C is performed using reactive ion etching.

20. The method of manufacturing of claim 19, further comprising the step of applying hydrofluoric acid to clean residue from the inside of the plurality of circular through holes, wherein the mesh frame comprises a plurality of circular through holes and the second layer of parylene-C has a thickness between 0.15 µm and 0.80 µm.

\* \* \* \* \*